(12) United States Patent
Nishimura et al.

(10) Patent No.: US 10,376,201 B2
(45) Date of Patent: Aug. 13, 2019

(54) CONTROL METHOD OF INFORMATION TERMINAL DEVICE, BODY MOVEMENT MEASURING DEVICE, AND RECORDING MEDIUM

(71) Applicant: Panasonic Intellectual Property Management Co., Ltd., Osaka (JP)

(72) Inventors: Kozo Nishimura, Osaka (JP); Masaaki Harada, Osaka (JP); Tomohiko Kitamura, Osaka (JP); Hiroko Sugimoto, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 56 days.

(21) Appl. No.: 15/399,974

(22) Filed: Jan. 6, 2017

(65) Prior Publication Data

US 2017/0202506 A1   Jul. 20, 2017

(30) Foreign Application Priority Data

Jan. 15, 2016 (JP) .................................. 2016-006682
Sep. 5, 2016 (JP) .................................. 2016-173196

(51) Int. Cl.
*A61B 5/00* (2006.01)
*A61B 5/11* (2006.01)
*G01H 17/00* (2006.01)

(52) U.S. Cl.
CPC .......... *A61B 5/4806* (2013.01); *A61B 5/1123* (2013.01); *A61B 5/6892* (2013.01); *A61B 5/7203* (2013.01); *A61B 5/7282* (2013.01); *G01H 17/00* (2013.01); *A61B 2562/0204* (2013.01)

(58) Field of Classification Search
CPC .......................... A61B 5/4806; A61B 5/1123
USPC ......................................................... 702/33
See application file for complete search history.

(56) References Cited

U.S. PATENT DOCUMENTS

| 7,396,331 | B2 * | 7/2008 | Mack | A61B 5/024 |
| | | | | 600/300 |
| 7,959,585 | B2 * | 6/2011 | Steenkeste | A61B 5/11 |
| | | | | 600/587 |
| 9,962,120 | B2 * | 5/2018 | Aoyama | A61B 5/486 |
| 2010/0016685 | A1 * | 1/2010 | Muehlsteff | A61B 5/02444 |
| | | | | 600/301 |

(Continued)

FOREIGN PATENT DOCUMENTS

JP      2006-181263      7/2006

*Primary Examiner* — Ricky Ngon
(74) *Attorney, Agent, or Firm* — Greenblum & Bernstein, P.L.C.

(57) ABSTRACT

A control method causes the processor to execute: excluding one or more pieces of first vibration data from a plurality of pieces of vibration data stored in the memory, wherein the plurality of pieces of vibration data are acquired within one period, wherein vibration times associated with the one or more pieces of first vibration data are included in an operation period in which the user performed the operation with respect to the information terminal device, and wherein the operation period is specified based on the time in the log information stored in the memory; and updating the threshold value using at least one piece of vibration data in the plurality of pieces of vibration data from which the one or more pieces of first vibration data are excluded.

10 Claims, 18 Drawing Sheets

(56) References Cited

U.S. PATENT DOCUMENTS

2010/0256512 A1\* 10/2010 Sullivan ................ A61B 5/113
  600/529
2016/0007870 A1\* 1/2016 Brueser ................ A61B 5/6892
  600/509

\* cited by examiner

| SCREEN OPERATIONS | BUTTON OPERATIONS | FOREGROUND APPLICATION OPERATIONS | START AND END OF TELEPHONE CALLS AND COMMUNICATIONS |
|---|---|---|---|
| SCREEN_ON | KEYCODE | RunningTaskList | Phone |
| SCREEN_OFF | HomeKey | ActivityManager | Mail |
| Scrolling | Lock | onCreate | RINGING |
| PanelView | onClick | onResume | Phonenumber is |
| ... | ... | (SPECIFIC APPLICATION NAME) | answerCall |
| ... | ... | ... | ... |

CONTROL METHOD OF INFORMATION TERMINAL DEVICE, BODY MOVEMENT MEASURING DEVICE, AND RECORDING MEDIUM

BACKGROUND

1. Technical Field

The present disclosure relates to a control method of an information terminal device provided with a vibration sensor, to a body movement measuring device, and to a recording medium.

2. Description of the Related Art

To date, body movement measuring devices have been disclosed that monitor the sleeping state of a sleeping person in order to comprehend the health condition of the sleeping person and so forth.

For example, in the body movement measuring device disclosed in Japanese Patent No. 4329690, sensors are installed in bedding and used to capture the lowest values of sensor values in real time, fluctuations in the lowest values of the sensor values are lessened by means of an exponential function to obtain a value that is set as a body movement determination threshold value, rough movement signals and slight movement signals are thereby separated, and the sleeping state of a sleeping person is determined. It is indicated that this body movement measuring device is able to determine the sleep of a sleeping person in a highly precise manner irrespective of the type and state of bedding and the body weight of the sleeping person. Here, a rough movement signal is a signal derived from a movement or the like of the body of the sleeping person such as falling asleep, getting out of bed, and turning over in bed, and a slight movement signal is a signal derived from the respiration and heart rate of the sleeping person.

Furthermore, in the body movement measuring device disclosed in Japanese Patent No. 4329690, it is indicated that an upper limit signal level is provided which is greater than the body movement determination threshold value and a set multiple of the body movement determination threshold value, the body movement determination threshold value is updated on the basis of vibration data that is equal to or less than the upper limit signal level, and it is thereby possible to suppress an increase in the body movement determination threshold value in the case where the sleeping person has clearly caused a rough movement.

However, a body movement measuring device that uses a vibration sensor of a general information terminal device (a smartphone, a mobile telephone terminal, or the like) is affected by the behavior of the sleeping person during nocturnal awakening. Thus, further investigation is required in order to realize highly precise sleep determination without being affected by the behavior of the sleeping person during nocturnal awakening.

SUMMARY

In one general aspect, the techniques disclosed here feature a control method of an information terminal device provided with a vibration sensor, a processor, and a memory. The control method causes the processor to execute: determining whether or not there is a body movement of a user on bedding on which the information terminal device has been placed, based on whether or not the magnitude of a vibration of the information terminal device indicated by vibration data detected by the vibration sensor is equal to or greater than a threshold value, acquiring the vibration data indicating the magnitude of the vibration of the information terminal device detected by the vibration sensor, and a vibration time indicating the time at which the vibration sensor detected the vibration of the information terminal device; associating the vibration time with the vibration data; storing vibration time and the associated vibration data in the memory; acquiring log information including the time at which an operation by the user was performed with respect to the information terminal device; storing the log information in the memory; excluding one or more pieces of first vibration data from a plurality of pieces of vibration data stored in the memory, wherein the plurality of pieces of vibration data are acquired within one period, wherein vibration times associated with the one or more pieces of first vibration data are included in an operation period in which the user performed the operation with respect to the information terminal device, and wherein the operation period is specified based on the time in the log information stored in the memory; and updating the threshold value using the plurality of pieces of vibration data from which the one or more pieces of first vibration data are excluded.

According to the aforementioned aspect, further improvement can be realized.

It should be noted that general or specific embodiments may be realized by means of a system, a method, an integrated circuit, a computer program, or a recording medium such as a computer-readable CD-ROM, and may be realized by an arbitrary combination of a system, a method, an integrated circuit, a computer program, and a recording medium.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

Figure 1:
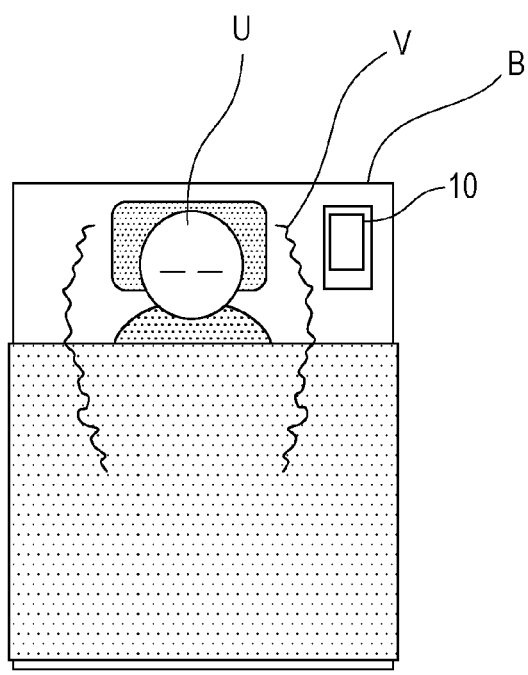
FIG. 1 is a conceptual diagram depicting a usage mode of an information terminal device in an embodiment.

DETAILED DESCRIPTION (Findings Forming the Basis of the Present Disclosure)

In recent years, it has been said that sleeping time has decreased due to changes in daily living habits in Japan, and that the level of satisfaction with sleep has declined. The sleep measuring device and so forth disclosed in Japanese Patent No. 4329690 have been developed from the need that users wish to comprehend their own sleeping states. However, to use the sleep measuring device disclosed in Japanese Patent No. 4329690, it is necessary for special sensors to be separately purchased and attached to bedding, and it is difficult for the sleep measuring device to be easily used from the aspects of cost, installation work, and so forth.

Furthermore, if consideration is given to applying the body movement measuring method disclosed in Japanese Patent No. 4329690 to a body movement measuring device that uses vibration sensors such as an acceleration sensor or gyro sensor housed within a general information terminal device (a smartphone, a mobile telephone terminal, or the like), the measurement precision of the sensors of the body movement measuring device disclosed in Japanese Patent No. 4329690 is high, and it is therefore possible for fluctuations in the lowest values of the sensors that indicate slight movement signals of the subject to be monitored and thereby separated from rough movement signals; however, the abovementioned vibration sensors of the information terminal device are affected by noise to a comparatively large extent, and it is therefore not possible to capture slight movement signals of the subject on the basis of fluctuations in the lowest values of the sensors. Consequently, the body movement measuring method disclosed in Japanese Patent No. 4329690 is not suitable for a body movement measuring device that uses the abovementioned vibration sensors of an information terminal device. Thus, for this kind of body movement measuring device, there is no choice but to adopt a method in which the body movement determination threshold value is determined on the basis of fluctuations in slight movement signals having large amplitude values from among vibration data.

In addition, in the body movement measuring device disclosed in Japanese Patent No. 4329690, an upper limit signal level that is a set multiple of the body movement determination threshold value is provided, and it is thereby possible to suppress, to an extent, the body movement determination threshold value being set high due to rough movements of the sleeping person; however, depending on the setting of the multiple, it may not be possible to remove rough movement signals that have a signal level the removal of which is desirable, and the precision of the body movement determination is liable to be affected.

It is desirable to provide a body movement measuring device that is able to solve these problems and also easily perform sleep determination in a highly precise manner with only a general information terminal device having a vibration sensor mounted therein owned by the user. To date, technical solutions for satisfying these demands have not been investigated.

A control method of an information terminal device according to an aspect of the present disclosure is a control method of an information terminal device provided with a vibration sensor, a processor, and a memory. The control method causes the processor to execute: determining whether or not there is a body movement of a user on bedding on which the information terminal device has been placed, based on whether or not the magnitude of a vibration of the information terminal device indicated by vibration data detected by the vibration sensor is equal to or greater than a threshold value; acquiring the vibration data indicating the magnitude of the vibration of the information terminal device detected by the vibration sensor, and a vibration time indicating the time at which the vibration sensor detected the vibration of the information terminal device; associating the vibration time with the vibration data; storing the vibration data and the associated vibration time in the memory; acquiring log information including the time at which an operation by the user was performed with respect to the information terminal device; storing the log information in the memory; excluding one or more pieces of first vibration data from a plurality of pieces of vibration data stored in the memory, wherein the plurality of pieces of vibration data are acquired within one period, wherein vibration times associated with the one or more pieces of first vibration data are included in an operation period in which the user performed the operation with respect to the information terminal device, and wherein the operation period is specified based on the time in the log information stored in the memory; and updating the threshold value using the plurality of pieces of vibration data from which the one or more pieces of first vibration data are excluded.

According to the abovementioned aspect, the threshold value, which is used to determine a body movement of a user, is updated using the plurality of pieces of vibration data from which the one or more pieces of first vibration data are excluded. One or more components of vibrations, which are different from the body movements made during sleep by the user, are included in the one or more pieces of first vibration data associated with variation times within the operation period. Thus, by removing the one or more pieces of first vibration data from the plurality of pieces of vibration data by means of the abovementioned method, the threshold value can be updated in an appropriate manner. As a result, it is possible to improve the precision of determining whether or not there is a body movement of the user by the information terminal device.

For example, in the excluding, one or more pieces of second vibration data may be further excluded from the plurality of pieces of vibration data. The vibration times associated with the one or more pieces of second vibration data may be included in a period immediately before or immediately after the operation period. Also, in the updating, the threshold value may be updated using the plurality of pieces of vibration data from which the one or more pieces of second vibration data are further excluded.

According to the abovementioned aspect, the threshold value is updated using the plurality of pieces of vibration data from which one or more pieces of second vibration data are further excluded. The vibration times associated with the one or more pieces of second vibration data are included in a period immediately before or immediately after the operation period in which it is determined that the user operated the information terminal device. In the period before the operation period, there is a possibility that the user may have moved his/her body in order to search for and prepare to operate the information terminal device, and in the period after the operation period, there is a possibility that the user may have moved his/her body in order to perform a movement to place the information terminal device on the bedding after having finished operating the information terminal device. Thus, one or more components of vibrations, which are different from the body movements made during sleep by the user, may be included in the one or more pieces of second vibration data associated with the variation times within the periods immediately before or immediately after the operation period. Therefore, by removing the one or more pieces of second vibration data form the plurality of pieces of vibration data by means of the abovementioned method, the threshold value can be updated in an even more appropriate manner.

For example, the control method further may cause the processor to execute: acquiring a device operation time from an electrical device by way of a network, wherein the device operation time is a time at which an operation has been performed by the user with respect to the electrical device in a house in which the bedding is arranged; and storing the device operation time in the memory. In the excluding, one or more pieces of third vibration data are further excluded from the plurality of pieces of vibration data, wherein vibration times associated with the one or more pieces of third vibration data are included in a device operation period in which the user performed the operation with respect to the electrical device, and the device operation period is specified based on the device operation time stored in the memory. In the updating, the threshold value is updated using the plurality of pieces of vibration data from which the one or more pieces of third vibration data are further excluded.

According to the abovementioned aspect, the threshold value is updated using the plurality of pieces of vibration data from which the one or more pieces of third vibration data are further excluded. One or more components of vibrations, which are different from the body movements made during sleep by the user, are included in the third vibration data associated with variation times within the device operation period. Therefore, by removing the one or more pieces of third vibration data from the plurality of pieces of vibration data, by means of the abovementioned method, the threshold value can be updated in an even more appropriate manner.

For example, in the excluding, one or more pieces of fourth vibration data may be further excluded from the plurality of pieces of vibration data. The vibration times associated with the one or more pieces of fourth vibration data may be included in a period immediately before or immediately after the device operation period. Also, in the updating, the threshold value may be updated using the plurality of pieces of vibration data from which the one or more pieces of fourth vibration data are further excluded.

According to the abovementioned aspect, the threshold value is updated using the plurality of pieces of vibration data from which one or more pieces of fourth vibration data are further extracted. In the period before the device operation period, there is a possibility that the user may have moved his/her body in order to search for and prepare to operate a remote control for the electrical device, and in the period after the device operation period, there is a possibility that the user may have moved his/her body in order to perform a movement to place the remote control in a predetermined location after having finished operating the remote control. Thus, one or more components of vibrations, which are different from the body movements made during sleep by the user, may be included in the one or more pieces of fourth vibration data associated with the variation times within the period immediately before or immediately after the device operation period. Therefore, by removing the one or more pieces of fourth vibration data from the plurality of pieces of vibration data by means of the abovementioned method, the threshold value can be updated in an even more appropriate manner.

For example, the control method may further cause the processor to execute: acquiring location information which indicates a location of the information terminal device; and storing a location change time, which indicates a time at which the location of the information terminal device changed, calculated based on the acquired location information. In the excluding, one or more pieces of fifth vibration data may be further excluded from the plurality of pieces of vibration data. The vibration times associated with the one or more pieces of fifth vibration data may be included in an out-of-bed period in which the information terminal device was located in a location that is different from the bedding. The out-of-bed period may be specified based on the location change time stored in the memory. In the updating, the threshold value may be updated using the plurality of pieces of vibration data from which the one or more pieces of fifth vibration data are further excluded.

According to the abovementioned aspect, the threshold value is updated using the plurality of pieces of vibration data from which the one or more pieces of fifth vibration data are further excluded. One or more components of vibrations, which are different from the body movements made during sleep by the user, are included in the one or more pieces of fifth vibration data associated with variation times within the out-of-bed period. Therefore, by removing the one or more pieces of fifth vibration data from the plurality of pieces of vibration data by means of the abovementioned method, the threshold value can be updated in an even more appropriate manner.

For example, in the excluding, one or more pieces of sixth vibration data may be further excluded from the plurality of pieces of vibration data. The vibration times associated with the one or more pieces of sixth vibration data may be included in a period immediately before or immediately after the out-of-bed period. In the updating, the threshold value may be updated using the plurality of pieces of vibration data from which the one or more pieces of sixth vibration data are further excluded.

According to the abovementioned aspect, the threshold value is updated using the plurality of pieces of vibration data from which one or more pieces of sixth vibration data are further extracted. In the periods immediately before and immediately after the out-of-bed period, there is a possibility that the user may hold the information terminal device and move his/her body in order to get out of bed or get into bed. Thus, one or more components of vibrations, which are different from the body movements made during sleep by the user, may be included in the one or more pieces of sixth vibration data associated with the variation times within the periods immediately before and immediately after the out-of-bed period. Therefore, by removing the one or more pieces of sixth vibration data from the plurality of pieces of vibration data by means of the abovementioned method, the threshold value can be updated in an even more appropriate manner.

For example, the processor may repeat the determining. The threshold value may be updated when the proportion of the number of times that the determination indicates a body movement of the user is present or absent, out of the number of times that the determination has been performed, has deviated from a predetermined appropriate range.

According to the abovementioned aspect, the information terminal device, after determining whether or not there is a body movement of the user using the threshold value, increases or decreases the threshold value on the basis of the result of that determination. Even if the body movements performed by the user are the same, the way in which vibrations propagate changes when the bedding is changed or when the placement surface changes due to a change in the placement location on the bedding, and therefore it may no longer be possible to appropriately determine whether or not there is a body movement of the user with the previously used threshold value. In such a case, by obtaining an appropriate threshold value using a determination result indicating whether or not there is a body movement on the new bedding or the new placement location on the bedding, the threshold value can be updated in an even more appropriate manner.

For example, an application program may be stored in the memory. The control method may further cause the processor to executes the application program. The log information may be generated by the executing application program when an operation by the user is performed with respect to the information terminal device.

According to the abovementioned aspect, the time, at which an operation by the user has been performed with respect to the information terminal device, can be specified specifically on the basis of log information generated by an application unit.

Furthermore, a body movement measuring device according to an aspect of the present disclosure is provided with: a vibration sensor that detects vibrations of the body movement measuring device; a memory; and a processor which: determines whether or not there is a body movement of a user on bedding on which the body movement measuring device has been placed, based on whether or not a magnitude of a vibration indicated by vibration data detected by the vibration sensor is equal to or greater than a threshold value; acquires the vibration data indicating the magnitude of the vibration detected by the vibration sensor, and a vibration time indicating a time at which the vibration sensor detected the vibration; associates the vibration time with the vibration data; stores the vibration time and the associated vibration data in the memory; acquires log information including a time at which an operation by the user was performed with respect to the body movement measuring device; stores the log information in the memory; excludes one or more pieces of first vibration data from a plurality of pieces of vibration data stored in the memory, wherein the plurality of pieces of vibration data are acquired within one period, wherein vibration times associated with the one or more pieces of first vibration data are included in an operation period in which the user performed the operation with respect to the information terminal device, and wherein the operation period is specified based on the time in the log information stored in the memory; and updates the threshold value using at least one piece of vibration data in the plurality of pieces of vibration data from which the one or more pieces of first vibration data are excluded.

The abovementioned aspect demonstrates an effect that is similar to that of the control method of an information terminal device.

Furthermore, a program according to an aspect of the present disclosure is a program for causing a computer to execute the abovementioned control method.

The abovementioned aspect demonstrates an effect that is similar to that of the control method of an information terminal device.

It should be noted that these comprehensive or specific aspects may be realized by a system, a method, an integrated circuit, a computer program, or a recording medium such as a computer-readable CD-ROM, and may be realized by an arbitrary combination of a system, a method, an integrated circuit, a computer program, or a recording medium.

Hereinafter, embodiments will be specifically described with reference to the drawings.

It should be noted that the embodiments described hereinafter all represent comprehensive or specific examples. The numerical values, the shapes, the constituent elements, the steps, the order of the steps, and the like given in the following embodiments are examples and are not intended to restrict the present disclosure. Furthermore, from among the constituent elements in the following embodiments, constituent elements that are not described in the independent claims indicating the most significant concepts are described as optional constituent elements. Furthermore, in all of the embodiments, it is also possible to combine the respective content thereof.

EMBODIMENTS

FIG. 1 is a conceptual diagram depicting a usage mode of an information terminal device 10 in the present embodiment.

As depicted in FIG. 1, the information terminal device 10 is placed on the bedding B of a user U. When the body of the user U moves, the information terminal device 10 vibrates due to vibrations V of the bedding B that occur together with the movement of the body of the user U. The information terminal device 10 is provided with a vibration sensor, and, when the information terminal device 10 vibrates due to the vibrations V of the bedding B, the vibration sensor detects vibrations of the information terminal device 10. In this way, the information terminal device 10 detects whether or not there is a body movement of the body of the user U.

Whether or not a body movement of the body of the user U is detected is used to control another electrical device. For example, in the case where the information terminal device 10 detects a body movement of the user U a predetermined number of times or more, the information terminal device 10 generates a signal for controlling another electrical device on the basis of the detection result, and transmits the generated signal.

The information terminal device 10 may transmit the generated signal for controlling the other electrical device, by way of a wired or wireless network. Furthermore, in the case where the other electrical device can be operated using a remote control (not depicted), the information terminal device 10 may transmit the signal for controlling the other electrical device to the remote control, and the remote control having received this signal may transmit the signal for controlling the other electrical device to the other electrical device.

Furthermore, the information terminal device 10 may transmit the detection result to the other electrical device. In this case, the other electrical device, when having received the detection result, may perform an operation based upon the detection result. For example, in the case where an air conditioner of the room in which the bedding B has been set up is the other electrical device, the information terminal device 10 can transmit the detection result to the air conditioner of the room in which the bedding B has been set up, and the air conditioner can perform control such as turning on air conditioning control of the air conditioner, on the basis of the received detection result. Furthermore, the information terminal device 10 may transmit the detection result to the remote control. For example, the information terminal device 10 transmits the detection result to the remote control that operates the air conditioner of the room in which the bedding B has been set up. The remote control, for example, can perform control such as transmitting a control signal for turning on the air conditioning control of the air conditioner, on the basis of the detection result.

Body movements of the user U being detected a predetermined number of times or more is thought to be due to the temperature or humidity of the room in which the bedding B has been set up not being comfortable for the user U, and the user U feeling that it is difficult to sleep. In this kind of case, an environment in which it is easy for the user U to sleep can be constructed by means of the air conditioning control of the air conditioner implemented by means of the information terminal device 10.

Furthermore, for example, information relating to the number of times that a body movement of the user U has been detected by the information terminal device 10 may be transmitted to a cloud server (not depicted) by way of a network. In this case, the cloud server accumulates received information regarding the number of times that a body movement of the user U has been detected. Alternatively, the cloud server may perform an operation that detects a body movement of the user U in the information terminal device 10.

In the case where a body movement of the user U has been detected a predetermined number of times or more, the cloud server may transmit a signal for controlling the other electrical device to the other electrical device or the remote control by way of a network.

Here, the vibrations V propagate from the body of the user U, through the bedding B, and reach the information terminal device 10. The way in which the vibrations V propagate changes depending on the type of bedding B (the material, weight, hardness, and the like of the contents thereof), the type of placement surface (the material, hardness, and the like) on which the bedding B has been placed, and so forth. Thus, the magnitudes of the vibrations detected by the information terminal device 10 fluctuate when the bedding B is changed and when the placement surface is changed due to the placement location of the bedding B being changed, even if the body movements of the user U are the same. In this kind of case, it is necessary for the information terminal device 10 to measure the body movements of the user U in an appropriate manner.

It should be noted that the information terminal device 10 may have a hardware configuration that is the same as a general information terminal device (a smartphone, a mobile telephone terminal, or the like) provided with a vibration sensor, or may be a dedicated device (also referred to as a body movement measuring device) provided with a general vibration sensor.

Figure 2:
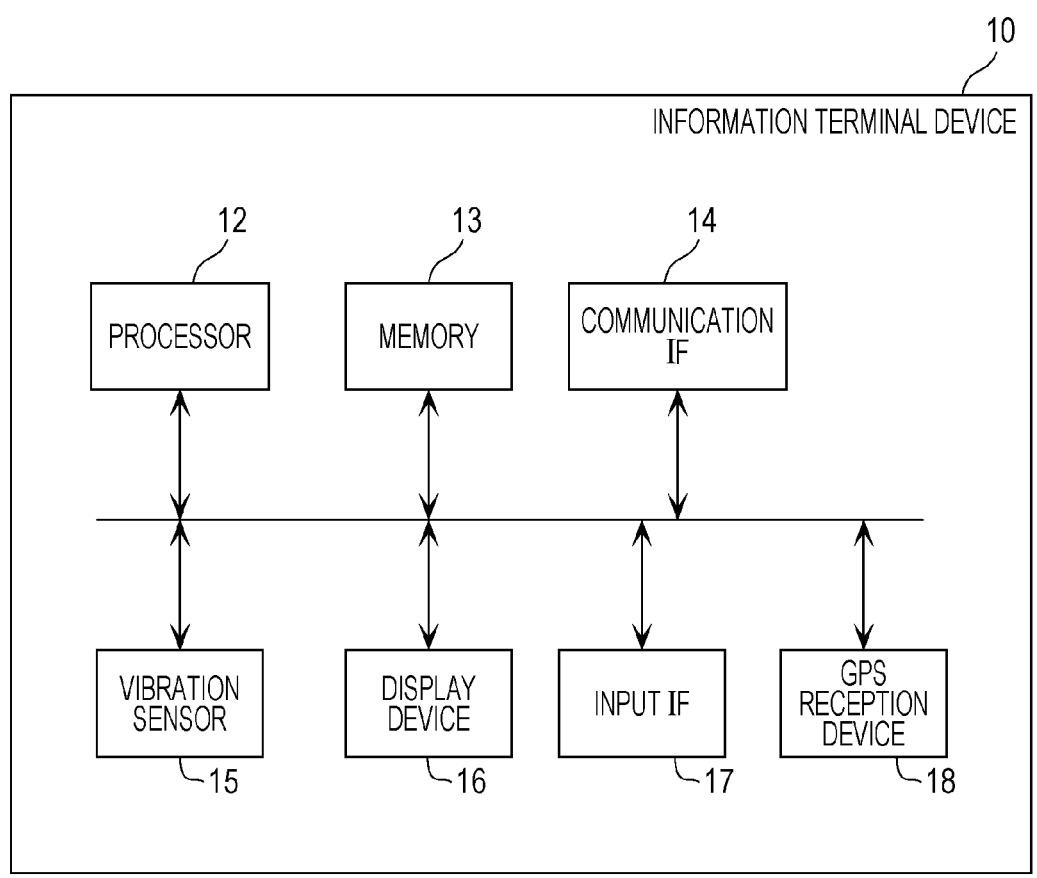
FIG. 2 is a block diagram depicting a hardware configuration of the information terminal device in the embodiment.

FIG. 2 is a block diagram depicting a hardware configuration of the information terminal device 10 in the present embodiment.

As depicted in FIG. 2, the information terminal device 10 is provided with a processor 12, a memory 13, a communication interface (IF) 14, a vibration sensor 15, a display device 16, and an input IF 17. Furthermore, the information terminal device 10 may be provided with a global positioning system (GPS) reception device 18.

The processor 12 is a processor that executes a control program stored in the memory 13 or the like. Processing executed by the information terminal device 10 is realized by the processor 12 executing the control program.

The memory 13 is a storage device that stores information, and has a volatile storage area that is used as a work area to be used when the processor 12 executes the control program, and a nonvolatile storage area in which the control program, data, and the like are stored.

The communication IF 14 is a communication interface that is connected to a network, and is for communicating with an external communication device by way of the network. The communication IF 14 is used when the information terminal device 10 performs a telephone call, an electronic mail, or Internet access either on the basis of an operation performed by the user U or automatically. The communication IF 14, for example, is realized by means of a mobile telephone communication interface (for example, a 3.5 generation mobile telecommunications system (3.5G) or a 3.9 generation mobile telecommunications system (3.9G)), a wired local area network (LAN) (for example, a wired LAN conforming with the IEEE 802.3 specification or Ethernet (registered trademark)), or a wireless LAN (for example, IEEE 802.11a, b, g, or n).

The vibration sensor 15 is a vibration sensor that detects vibrations of the information terminal device 10, and outputs vibration data that indicates the magnitudes of the detected vibrations. The vibration sensor 15, specifically, has at least one of an acceleration sensor that detects acceleration, a gyro sensor that detects angular velocity, and an angle sensor that detects an angle formed with a reference angle, for example. It should be noted that the abovementioned vibrations include not only vibrations serving as periodic movements centered on one location, but also physical quantities that can be acquired by the abovementioned sensors, such as changes in location or changes in angle, for example.

The display device 16 is a display device that displays information or the like as an image. The display device 16 is a liquid crystal display, for example, or, more specifically, is a display portion of a touch panel display.

The input IF 17 is an input interface that receives operations by the user U. The input IF 17, for example, is a touch panel, a touch pad, or a button, or, more specifically, is a touch panel portion of a touch panel display.

The GPS reception device 18 is a GPS device that receives signals from a GPS satellite, and outputs location information indicating the location on the Earth of the information terminal device 10.

Figure 3:
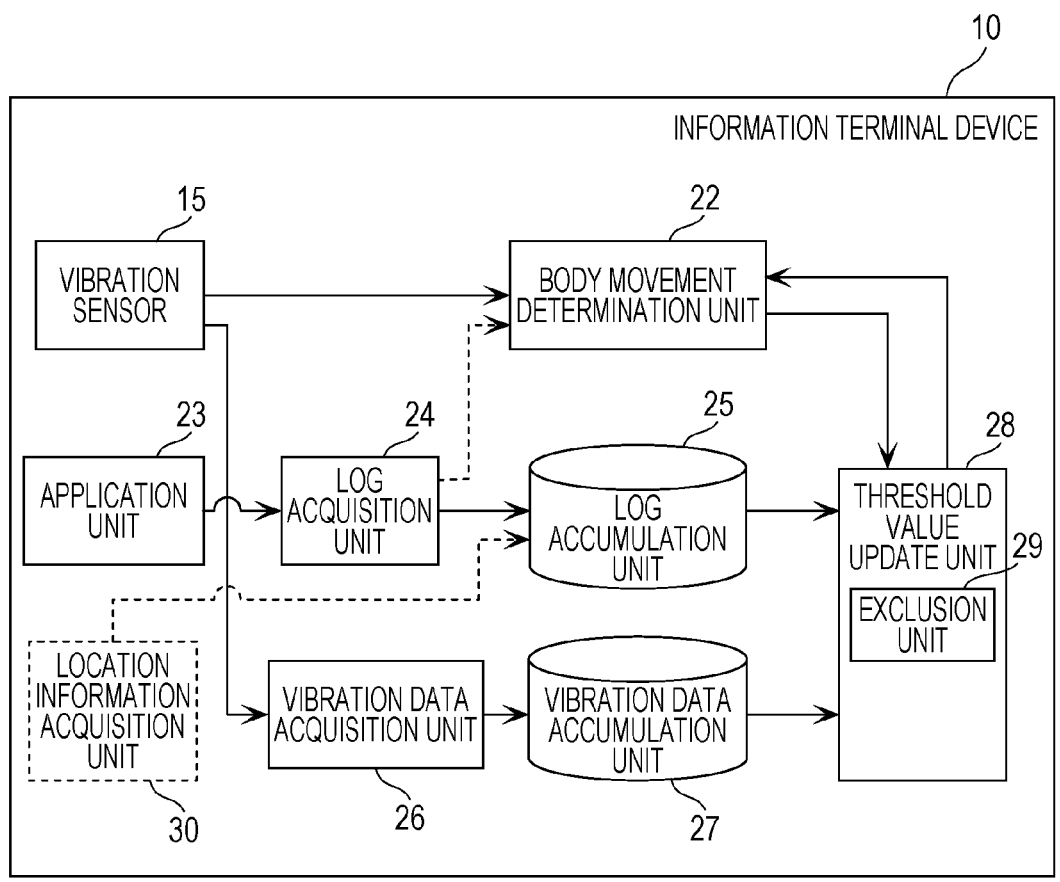
FIG. 3 is a block diagram depicting a functional configuration of the information terminal device in the embodiment.
Figure 4:
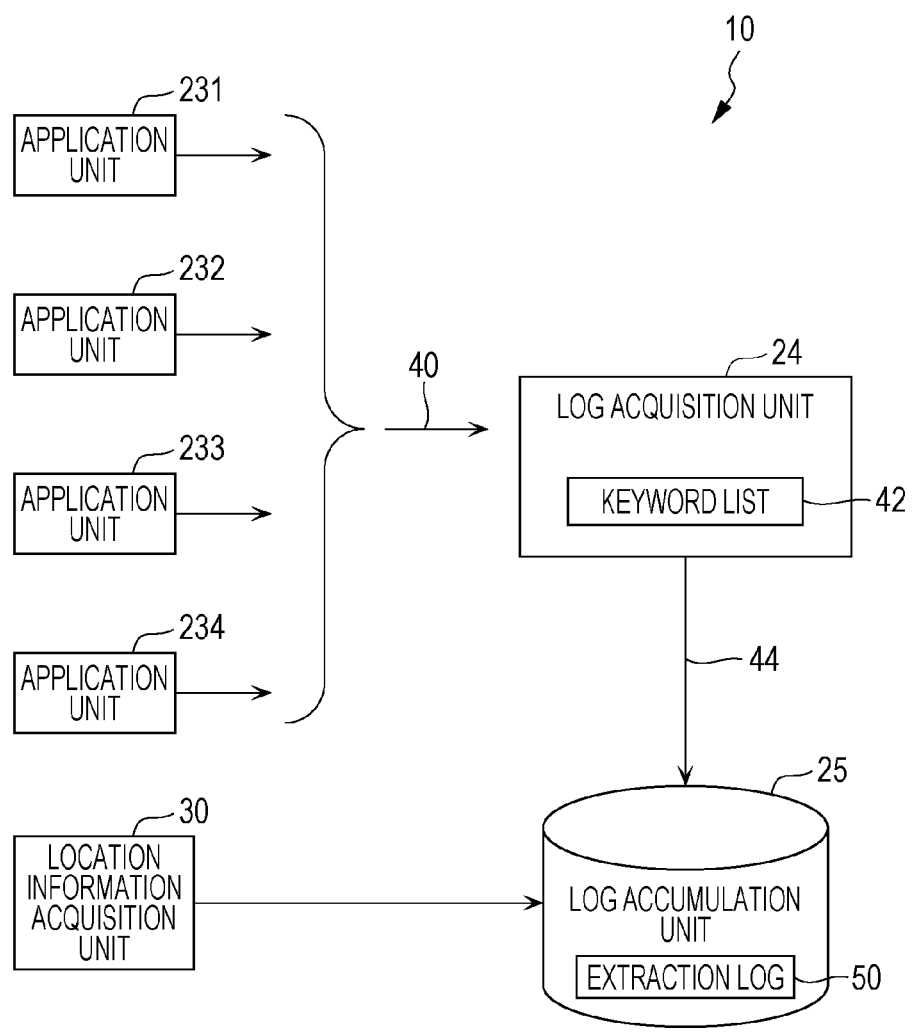
FIG. 4 is an explanatory diagram depicting a method for accumulating logs implemented by the information terminal device in the embodiment.

FIG. 3 is a block diagram depicting a functional configuration of the information terminal device 10 in the present embodiment. FIG. 4 is an explanatory diagram depicting a method for accumulating logs implemented by the information terminal device 10 in the present embodiment. A functional configuration of the information terminal device 10 will be described with reference to these diagrams.

As depicted in FIG. 3, the information terminal device 10 is provided with a body movement determination unit 22, an application unit 23, a log acquisition unit 24, a log accumulation unit 25, a vibration data acquisition unit 26, a vibration data accumulation unit 27, and a threshold value update unit 28. The threshold value update unit 28 has an exclusion unit 29. Furthermore, the information terminal device 10 may be provided with a location information acquisition unit 30.

It should be noted that the abovementioned constituent elements may be logical function blocks realized by the processor 12 executing a program, or may be physical function blocks configured by means of dedicated circuits. It should be noted that the vibration sensor 15 depicted in FIG. 3 is the vibration sensor 15 depicted in FIG. 2.

The body movement determination unit 22 is a processing unit that determines whether or not there is a body movement of the user U on the bedding B on which the information terminal device 10 has been placed. Specifically, the body movement determination unit 22 acquires the magnitudes of vibrations indicated by vibration data detected by the vibration sensor 15. The magnitude of a vibration is a quantity that is 0 when there are no vibrations and becomes a larger value as the vibrations increase, and, for example, is calculated by an acceleration, angular velocity, or angle detected by the vibration sensor 15 taking a square value or an absolute value as necessary. The body movement determination unit 22 then determines whether or not there is a body movement of the user U on the bedding B on which the information terminal device 10 has been placed, on the basis of whether or not the magnitudes of the vibrations detected by the vibration sensor 15 are equal to or greater than a predetermined threshold value. A body movement of the user U is produced by the user U asleep on the bedding B turning over in bed, for example. Thus, the information terminal device 10 can detect the user U turning over in bed by determining whether or not there is a body movement of the user U.

Furthermore, the body movement determination unit 22 outputs a determination result regarding whether or not there is a body movement of the user U, specifically, "body movement present" or "body movement not present". The output information is used to control another electrical device as mentioned above, for example.

Furthermore, the body movement determination unit 22 possesses the abovementioned threshold value that is used when detecting whether or not there is a body movement of the user U. This threshold value may be determined by pre-measurement in initialization processing described hereinafter, and may be set to a suitable value in advance. Furthermore, this threshold value is updated by the threshold value update unit 28.

The application unit 23 is a processing unit that is realized by a program executed by the information terminal device 10, and exhibits a predetermined function. The application unit 23, for example, is realized by the processor 12 executing a telephone transmission/reception program, an electronic mail transmission/reception program, or an Internet browser program. The application unit 23 outputs predetermined log information (hereinafter, also simply referred to as a log; corresponding to log 40 of FIG. 4) to a console in accordance with an operating status. The log 40 is configured from one or more rows with each row including an operation performed with respect to the application unit 23 and the time at which the operation was performed, for example, and including information indicating the operating status of the application unit 23 or an event, and the time at which the log 40 was output. A specific example of the log 40 will be described in detail hereinafter. It should be noted that there may be a plurality of application units 23 such as the application units 231, 232, 233, and 234 depicted in FIG. 4.

The log acquisition unit 24 is a processing unit that acquires the log 40 output to the console by the application unit 23. The log acquisition unit 24 extracts items satisfying predetermined conditions from within the log 40 output to the console by the application unit 23, and stores an extracted log (hereinafter, also referred to as an extraction log; corresponding to extraction log 44 of FIG. 4) in the log accumulation unit 25.

Specifically, the log acquisition unit 24 has a keyword list 42 that corresponds to the predetermined conditions. The keyword list 42 includes one or more keywords that are included in rows to be accumulated in the log accumulation unit 25 by the log acquisition unit 24, from among the rows included in the log 40. The log acquisition unit 24 acquires the log 40 output to the console by the application unit 23, determines whether or not each row included in the log 40 includes the keywords included in the keyword list 42, and extracts the rows that include the keywords included in the keyword list 42 from among the rows included in the log 40. The log acquisition unit 24 then provides the extracted log to the log accumulation unit 25 as the extraction log 44. The extraction log 44, for example, includes information items indicating whether the display of the display device 16 of the information terminal device 10 is on or off, operations with respect to the input IF 17, operations of foreground applications of the information terminal device 10, telephone calls and communications, and wireless communication environments.

It should be noted that the keyword list 42 may be stored in the memory 13. In such a case, the log acquisition unit 24 reads out the keyword list 42 stored in the memory 13 and uses this for the abovementioned determination.

The log accumulation unit 25 is a storage unit that accumulates and stores logs output to the console by the application unit 23. The log accumulation unit 25 acquires the extraction log 44 from the log acquisition unit 24, and stores this as an extraction log 50. The extraction log 50 is read out from the log accumulation unit 25 by the exclusion unit 29. The log accumulation unit 25 is realized by the memory 13.

The vibration data acquisition unit 26 is a processing unit that acquires a piece of vibration data and vibration time, that associates the piece of vibration data with the vibration time and that stores the piece of vibration data and the associated vibration time in the vibration data accumulation unit 27. The piece of vibration data is, for example, a magnitude of a vibration detected by the vibration sensor 15, namely the piece of vibration data is output by the vibration sensor 15. The vibration time is a time at which the vibration sensor detected the vibration. The vibration data acquisition unit 26 repeatedly acquires a piece of vibration data at predetermined cycles (for example, cycles of 10 times per second).

It should be noted that, when storing the piece acquired vibration data in the vibration data accumulation unit 27, the vibration data acquisition unit 26 may, in addition, separately store N pieces of vibration data starting from vibrations having large magnitudes from among the vibration data to be stored. When this approach is taken, there is an advantage in that it is possible to reduce the load of processing to extract N pieces of vibration data starting from vibrations having large magnitudes when the threshold value update unit 28 described hereinafter updates the threshold value.

The vibration data accumulation unit 27 is a storage unit that accumulates and stores the vibration times and the associated magnitudes of vibrations detected by the vibration sensor 15. The vibration data accumulation unit 27 has a plural of pieces of vibration data stored therein by the vibration data acquisition unit 26, and has vibration data read out therefrom by the exclusion unit 29. The vibration data accumulation unit 27 is realized by the memory 13.

The threshold value update unit 28 is a processing unit that updates the threshold value used in the determination by the body movement determination unit 22, using one or more pieces of vibration data acquired within a predetermined measurement period, from among a plurality of pieces of vibration data stored by the vibration data accumulation unit 27. Updating of the threshold value is, for example, executed when the number of times that "body movement present" or "body movement not present" has been determined in the determination by the body movement determination unit 22 has deviated from an appropriate range, and the threshold value is increased or decreased in such a way that the number of times that "body movement present" or "body movement not present" is determined in the determination by the body movement determination unit 22 approaches the appropriate range. A method investigated in the past can be used for the threshold value update processing, and an example thereof will be described hereinafter. It should be noted that the measurement period is one day or one week, for example.

The exclusion unit 29 is a processing unit that excludes one or more pieces of vibration data from a plurality of pieces of vibration data of which time are included in the measurement period. Specifically, the exclusion unit 29 specifies an operation period in which the user performed the operation with respect to the information terminal based on a time stored by the vibration data accumulation unit 27. The exclusion unit 29 specifies one or more pieces of vibration data (referred to as first vibration data) associated with vibration times included in the operation period. The exclusion unit 29 excludes the one or pieces of first vibration data from the plurality of pieces of vibration data. The threshold value update unit 28 updates the threshold value using the plurality of pieces of vibration data from which the one or more pieces of first vibration data are excluded. Also, the exclusion unit 29 may update the threshold value using the plurality of pieces of vibration data from which the one or more pieces of first vibration data are excluded.

It should be noted that the exclusion unit 29 may further exclude one or more pieces of vibration data (referred to as second vibration data), associated with vibration time which is included in at least one of periods immediately before and immediately after the operation period, from the plurality of pieces of vibration data. The threshold value update unit 28 updates the threshold value using the plurality of pieces of vibration data from which the one or more pieces of the second vibration data are further excluded. Also, the exclusion unit 29 may update the threshold value using the plurality of pieces of vibration data from which the one or more pieces of second vibration data are further excluded.

It should be noted that the exclusion unit 29 may specify a device operation period in which the user performed the operation with respect to the electrical device in a house in which the bedding is arranged. The exclusion unit 29 may specify the device operation period based on the device operation time. The device operation time is a time at which an operation has been performed by the user with respect to the electrical device. The device operation time may be stored in the log accumulation unit 25.

The exclusion unit 29 may exclude one or pieces of vibration data (referred to as third vibration data), associated with vibration times included in the device operation period, from the plural pieces of vibration data in the measurement period.

The threshold value update unit 28 may update the threshold value using the plurality of pieces of vibration data from which the one or more pieces of third vibration data are further excluded. Also, the exclusion unit 29 may update the threshold value using the plurality of pieces of vibration data from which the one or more pieces of third vibration data are further excluded.

The exclusion unit 29 may further exclude one or more pieces of vibration data (referred to as fourth vibration data), associated with vibration time which is included in at least one of periods immediately before and immediately after the device operation period, from the plurality of pieces of vibration data. The threshold value update unit 28 updates the threshold value using the plurality of pieces of vibration data from which the one or more pieces of the fourth vibration data are further excluded. Also, the exclusion unit 29 may update the threshold value using the plurality of pieces of vibration data from which the one or more pieces of fourth vibration data are further excluded.

Also, location information, which indicates a location of the information terminal device, may be stored in the log accumulation unit 25. Also a time, at which the location information is acquired, may be stored in the log accumulation unit 25. The exclusion unit 29 may specify an out-of-bed period based on the location information and the time stored in the log accumulation unit 25. The out-of-bed period is a period in which the information terminal device was located in a location that is different from on the bedding. The exclusion unit 29 may calculate may calculate a location change time based on the location information and the time. The location change time is a time, which indicates a time at which the location of the information terminal device changed. It should be noted that the exclusion unit 29 may further exclude one or pieces of vibration data (referred to as fifth vibration data), associated with vibration times included in the out-of-bed period. The threshold value update unit 28 may update the threshold value using the plurality of pieces of vibration data from which the one or more pieces of fifth vibration data are further excluded. Also, the exclusion unit 29 may update the threshold value using the plurality of pieces of vibration data from which the one or more pieces of fifth vibration data are further excluded.

The exclusion unit 29 may further exclude one or more pieces of vibration data (referred to as sixth vibration data), associated with vibration time which is included in at least one of periods immediately before and immediately after the out-of-bed period, from the plurality of vibration data. The threshold value update unit 28 updates the threshold value using the plurality of pieces of vibration data from which the one or more pieces of the sixth vibration data are further excluded. Also, the exclusion unit 29 may update the threshold value using the plurality of pieces of vibration data from which the one or more pieces of sixth vibration data are further excluded.

The location information acquisition unit 30 is a processing unit that repeatedly acquires, at predetermined cycles, location information indicating the location of the information terminal device 10, and outputs the acquired location information and a time at which the location information is acquired. The location information and the time output by the location information acquisition unit 30 is stored in the log accumulation unit 25. The location information acquired by the location information acquisition unit 30 does not need to be absolute location information and may be relative location information, and it is also possible to use a value that changes according to changes in the location of the information terminal device 10.

Various methods are possible for the location information acquisition unit 30 to acquire the location information. For example, the location information acquisition unit 30 may acquire location information indicating the location on the Earth of the information terminal device 10, output by the GPS reception device 18. Location information indicating the location on the Earth corresponds to the abovementioned absolute location information. Furthermore, in the case where the communication IF 14 is a wireless communication interface, the location information acquisition unit 30 may acquire changes in the location of the information terminal device 10 on the basis of changes in the reception signal strength of radio waves that arrive from another wireless communication device. For example, in the case where the communication IF 14 is a wireless LAN, the communication IF 14 is able to continuously acquire the reception signal strength of beacon signals transmitted by an access point, and detect the movement of the information terminal device 10 on the basis of changes in the acquired reception signal strength.

Figure 5:
FIG. 5 is an explanatory diagram depicting examples of keywords included in logs output by the information terminal device in the embodiment.

FIG. 5 is an explanatory diagram depicting examples of keywords included in logs output by the information terminal device 10 in the present embodiment.

As depicted in FIG. 5, the keywords include keywords relating to screen operations, button operations, foreground application operations, and the start and end of telephone calls and communications.

Keywords relating to screen operations include "SCREEN_ON" which is a keyword included in a log that is output when the display device 16 has transitioned from a state in which a screen is not displayed to a state in which a screen is displayed, "SCREEN_OFF" which is a keyword included in a log that is output when the display device 16 has transitioned from a state in which a screen is displayed to a state in which a screen is not displayed, and the like.

Keywords relating to button operations include "KEY-CODE" which is a keyword included in a log indicating the key code of a key operated by the user U, "HomeKey" which is a keyword included in a log indicating that a home key has been pressed, and the like.

Keywords relating to foreground application operations include "RunningTaskList" which is a keyword included in a log that is output when a process or task being executed by the information terminal device 10 is confirmed, "Activity-Manager" which is a keyword included in a log that is output when the state of the process or task is acquired, and the like.

Keywords relating to the start and end of telephone calls and communications include "Phone" which is a keyword included in a log that is output when a telephone call is started, "Mail" which is a keyword included in a log that is output when an electronic mail is transmitted, and the like.

Figure 6:
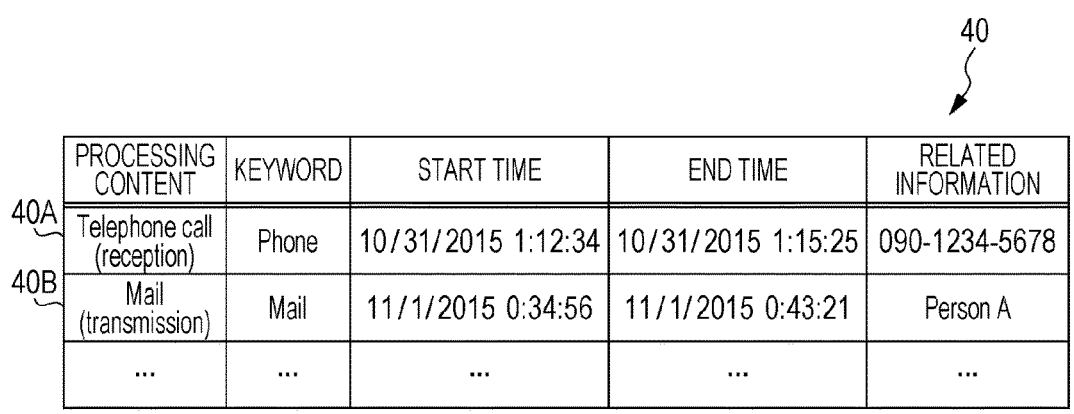
FIG. 6 is an explanatory diagram depicting examples of information included in logs output by the information terminal device in the embodiment.

FIG. 6 is an explanatory diagram depicting an example of the log 40 output by the information terminal device 10 in the present embodiment. The log 40 is information that is output on the basis of an operation performed by the user U with respect to the information terminal device 10, and includes information indicated in the columns of "processing content", "keyword", "start time", "end time", and "related information".

The "processing content" column indicates the content of processing executed by the information terminal device 10 on the basis of an operation by the user U. The "processing content" column corresponds to the information in the "keyword" column described hereinafter, and can therefore be decided from the information in the "keyword" column.

The "keyword" column indicates a keyword that represents processing executed by the information terminal device 10 on the basis of an operation by the user U. The keyword indicated in the "keyword" column corresponds to the processing content of the information terminal device 10. The keyword indicated in the "keyword" column is one keyword from among the keywords included in the keyword list 42 depicted in FIG. 5.

The "start time" and "end time" columns indicate times at which processing executed by the information terminal device 10 on the basis of an operation by the user U has started and ended, respectively.

The "related information" column indicates information relating to the processing executed by the information terminal device 10 on the basis of an operation by the user U.

The log 40A is an example of a log that is output when telephone call (reception) processing is started at 1:12:34 on 10/31/2015 and ended at 1:15:25 on 10/31/2015 by the information terminal device 10 on the basis of operations by the user U, and the terminal number of the telephone call counterpart is "090-1234-5678", for example.

Furthermore, the log 40B is an example of a log that is output when electronic mail transmission processing is started at 0:34:56 on 11/1/2015 and ended at 0:43:21 on 11/1/2015 by the information terminal device 10 on the basis of operations by the user U, and the destination of the electronic mail is "person A".

Next, processing to exclude vibration data performed by the exclusion unit 29 will be specifically described.

Figure 7:
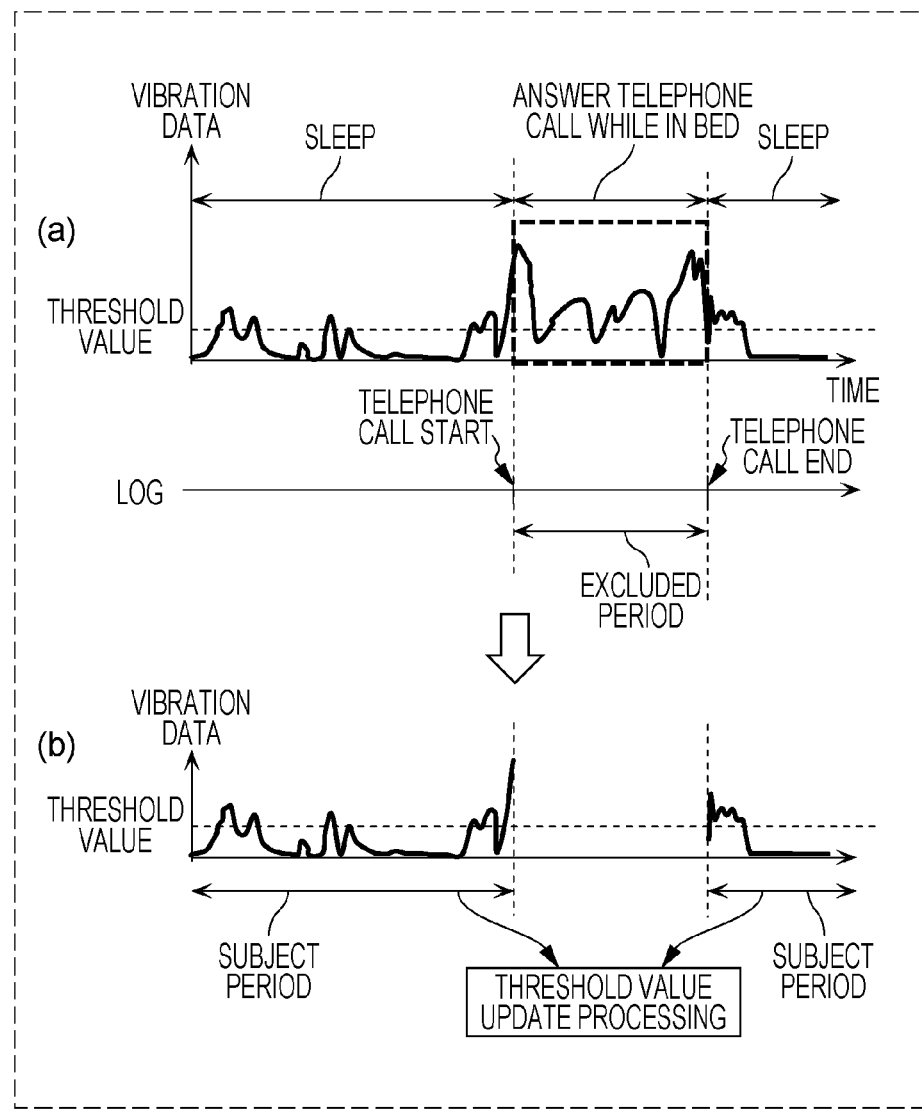
FIG. 7 is an explanatory diagram depicting a first example of a method for excluding vibration data implemented by an exclusion unit in the embodiment.

FIG. 7 is an explanatory diagram depicting a first example of a method for excluding vibration data implemented by the exclusion unit 29 in the present embodiment. This exclusion method is a method for excluding vibration data included in an operation period in which the user U has performed an operation with respect to the information terminal device 10.

The vibration data depicted in FIG. 7(*a*) is data indicating changes over time in the magnitudes of vibrations acquired by the vibration sensor 15 and the vibration data acquisition unit 26 of the information terminal device 10 placed on the bedding B. The vibration data indicated in FIG. 7(*a*) includes a series of vibration data for the case where the user U has initially been sleeping on the bedding B, then received a telephone call by means of the information terminal device 10 while still in bed, and thereafter fallen asleep. It is apparent that the magnitudes of the vibrations detected by the vibration sensor 15 are comparatively small when the user U is asleep, and are comparatively large when the user U is receiving the telephone call. This is because, when the user U is asleep, the vibration sensor 15 detects vibrations produced by motions such as turning over in bed performed occasionally by the user U, and, when the user U is receiving the telephone call, the vibration sensor 15 detects vibrations produced by head and hand movements and the like of the user U who is awake.

Furthermore, the log depicted in FIG. 7(a) indicates a log that was output by the information terminal device 10 in the period in which the abovementioned vibration data was acquired. This log includes a telephone call start time and a telephone call end time. These are more or less consistent with the times at which the user U started and ended the abovementioned reception of the telephone call.

The exclusion unit 29 generates vibration data (FIG. 7(b)) for a period (also referred to as a subject period) having had excluded therefrom the period (also referred to as an excluded period) from the telephone call start time to the telephone call end time in the log, from among the vibration data depicted in FIG. 7(a). Thereafter, the threshold value update unit 28 performs threshold value update processing using the vibration data depicted in FIG. 7(b), namely the vibration data of the subject period.

In this way, the threshold value update unit 28 updates the threshold value that is used in the determination by the body movement determination unit 22, excluding vibrations produced when the user U is considered to be awake. Thus, by excluding vibrations produced when the user U is considered to be awake, the threshold value update unit 28 is able to appropriately update the threshold value using vibrations produced when the user U is asleep.

Figure 8:
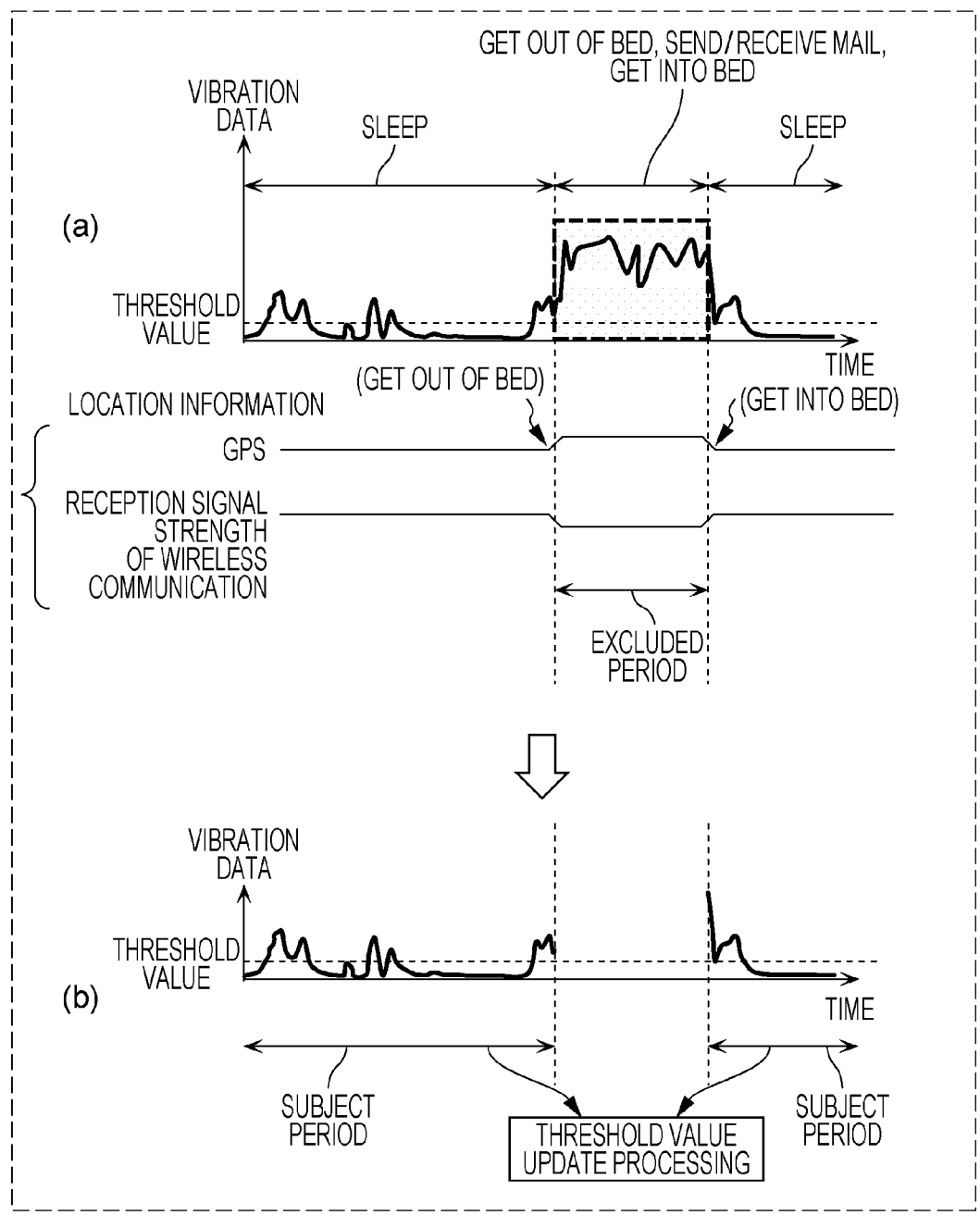
FIG. 8 is an explanatory diagram depicting a second example of a method for excluding vibration data implemented by the exclusion unit in the embodiment.

FIG. 8 is an explanatory diagram depicting a second example of a method for excluding vibration data implemented by the exclusion unit 29 in the present embodiment. This exclusion method is a method for excluding vibration data included in an out-of-bed period in which the information terminal device 10 was located in a location that is different from on the bedding B.

The vibration data depicted in FIG. 8(a) is data indicating changes over time in the magnitudes of vibrations acquired by the vibration sensor 15 and the vibration data acquisition unit 26 of the information terminal device 10 placed on the bedding B. The vibration data indicated in FIG. 8(a) includes a series of vibration data for the case where the user U has initially been sleeping, then gotten out of bed, performed a mail transmission/reception operation in a location that is different from on the bedding B, and thereafter gotten into bed and fallen asleep. Here, getting out of bed refers to moving to another location from on the bedding B, and getting into bed refers to moving from another location to on the bedding B.

It is apparent that the magnitudes of the vibrations detected by the vibration sensor 15 are comparatively small when the user U is asleep, and are comparatively large when the user U gets out of bed, transmits/receives mail, and gets into bed. This is because, when the user U is asleep, the vibration sensor 15 detects vibrations produced by motions such as turning over in bed performed occasionally by the user U, and, when the user U gets out of bed, transmits/receives mail, and gets into bed, the vibration sensor 15 detects vibrations produced by movements and the like of various parts of the body including the head and hands of the user U.

Furthermore, the location information depicted in FIG. 8(a) indicates location information that was output by the information terminal device 10 in the period in which the abovementioned vibration data was acquired. The location information output by the GPS reception device 18 and changes in the reception signal strength acquired by the communication IF 14 serve as examples of this location information. It should be noted that the exclusion method described here uses at least one of the location information output by the GPS reception device 18 and the changes in the reception signal strength acquired by the communication IF 14.

The location information output by the GPS reception device 18 and the changes in the reception signal strength acquired by the communication IF 14 include changes that occur together with changes in the location of the information terminal device 10. These changes are more or less consistent with the points in time when the user U has gotten out of bed and gotten into bed.

The exclusion unit 29 generates vibration data (FIG. 8(b)) for a period (also referred to as a subject period) having had excluded therefrom a period (also referred to as an excluded period) from the point in time when the user U got out of bed to the point in time when the user U got into bed, determined from changes in the location information, from among the vibration data depicted in FIG. 8(a). Thereafter, the threshold value update unit 28 performs threshold value update processing using the vibration data depicted in FIG. 8(b), namely the vibration data of the subject period.

Figure 9:
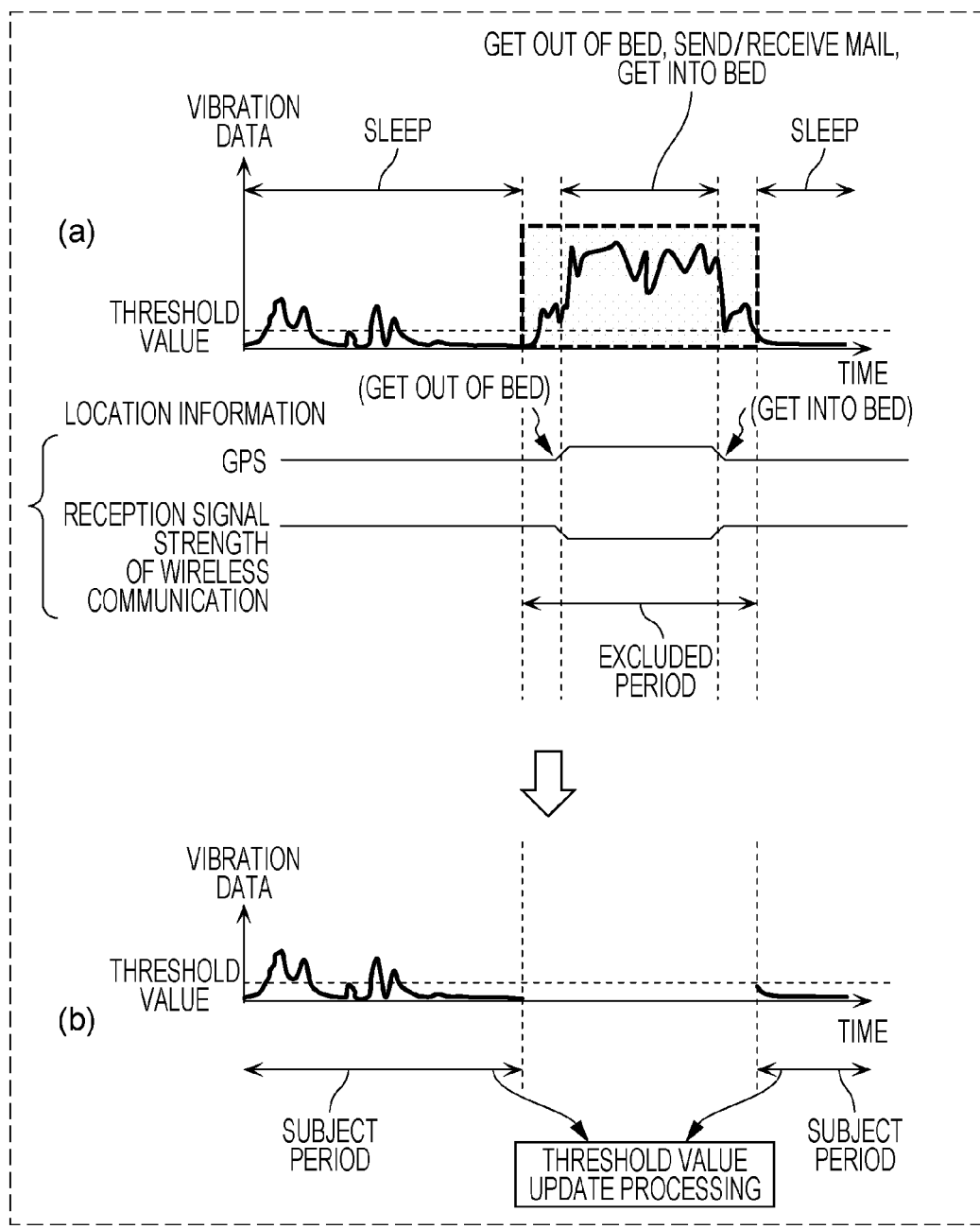
FIG. 9 is an explanatory diagram depicting a third example of a method for excluding vibration data implemented by the exclusion unit in the embodiment.

FIG. 9 is an explanatory diagram depicting a third example of a method for excluding vibration data implemented by the exclusion unit 29 in the present embodiment. This exclusion method is a method for excluding vibration data included in a predetermined period that includes the out-of-bed period.

The vibration data depicted in FIG. 9(a) is the same as the vibration data depicted in FIG. 8(a).

The location information depicted in FIG. 9(b) is the same as the location information depicted in FIG. 8(b), but the method for setting the excluded period and the subject period is different.

In this exclusion method, the exclusion unit 29 generates vibration data (FIG. 9(b)) having had excluded therefrom a period from a predetermined time prior to the user U getting out of bed to a predetermined time subsequent to the user U getting into bed, determined from changes in the location information, from among the vibration data depicted in FIG. 9(a). That is, a predetermined period that includes the period from the point in time when the user U got out of bed to the point in time when the user U got into bed is set as the excluded period. It should be noted that the abovementioned predetermined time may be approximately two to three minutes, or may be approximately 10 minutes. Furthermore, the length of the predetermined time before getting out of bed and the length of the predetermined time after getting into bed may be different.

Thereafter, the threshold value update unit 28 performs threshold value update processing using the vibration data depicted in FIG. 9(b), namely the vibration data of the subject period.

It should be noted that if the "out-of-bed period" in the above explanation is substituted with "operation period", it is also possible to exclude vibration data included in a predetermined period that includes the operation period.

Processing executed by the information terminal device 10 configured as mentioned above will be described hereinafter.

Figure 10:
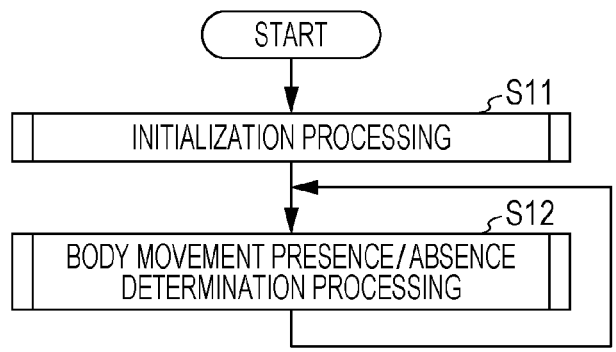
FIG. 10 is a flow diagram depicting an overview of processing relating to determining whether or not there is a body movement, executed by the information terminal device in the embodiment.

FIG. 10 is a flow diagram depicting an overview of processing relating to determining whether or not there is a body movement, executed by the information terminal device 10 in the present embodiment.

In step S11, the body movement determination unit 22 performs initialization processing. Initialization processing is processing for deciding the threshold value to be used in processing performed thereafter for determining whether or not there is a body movement. The detailed processing included in the initialization processing will be described in detail hereinafter.

In step S12, the body movement determination unit 22 performs body movement presence/absence determination processing. The body movement presence/absence determination processing is processing for determining whether or not there is a body movement of the user U on the bedding B on which the information terminal device 10 has been placed. The detailed processing included in the body movement presence/absence determination processing will be described in detail hereinafter.

Once step S12 has ended, the information terminal device 10 executes step S12 once again. That is, the information terminal device 10 repeatedly executes step S12. The time interval at which step S12 is executed is the interval (for example, 10 msec) at which the body movement determination unit 22 acquires vibration data from the vibration sensor 15.

Figure 11:
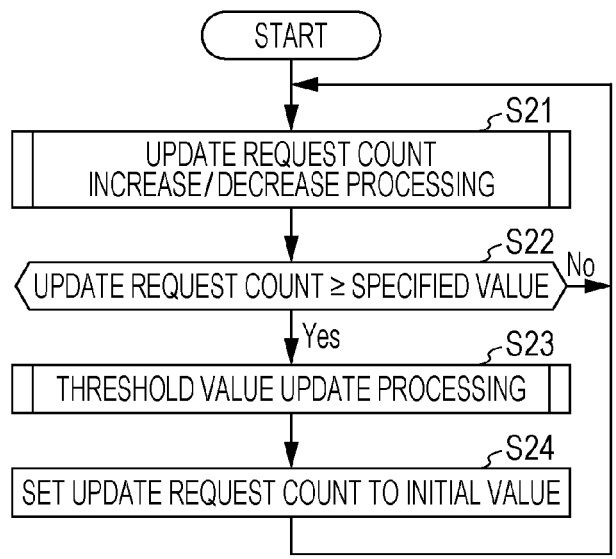
FIG. 11 is a flow diagram depicting an overview of threshold value update processing executed by the information terminal device in the embodiment.

FIG. 11 is a flow diagram depicting an overview of threshold value update processing executed by the information terminal device 10 in the present embodiment.

In step S21, the body movement determination unit 22 performs update request count increase/decrease processing. Update request count increase/decrease processing is processing for increasing or decreasing an update request count, which is the degree to which it is necessary to update the threshold value, on the basis of the validity of a determination result reached by the body movement determination unit 22. The detailed processing included in the update request count increase/decrease processing will be described in detail hereinafter.

In step S22, the body movement determination unit 22 determines whether or not the update request count that has been increased or decreased in step S21 is equal to or greater than a specified value. In the case where it has been determined in step S22 that the update request count is equal to or greater than the specified value (yes in step S22), processing advances to step S23. However, in the case where it has been determined in step S22 that the update request count is less than the specified value (no in step S22), the information terminal device 10 executes step S21 once again.

In step S23, the threshold value update unit 28 performs threshold value update processing. Threshold value update processing is processing for updating the threshold value that is used for determining whether or not there is a body movement by the body movement determination unit 22. The detailed processing included in the threshold value update processing will be described in detail hereinafter.

In step S24, the threshold value update unit 28 sets the update request count to an initial value (for example, zero).

Once step S24 has ended, the information terminal device 10 executes step S21 once again.

It should be noted that the time interval at which the information terminal device 10 executes step S21 is every one day or every one week, for example. More specifically, for example, the information terminal device 10 executes step S21 at 12:00 midday every day or at 12:00 midday on a specific day of the week.

Figure 12:
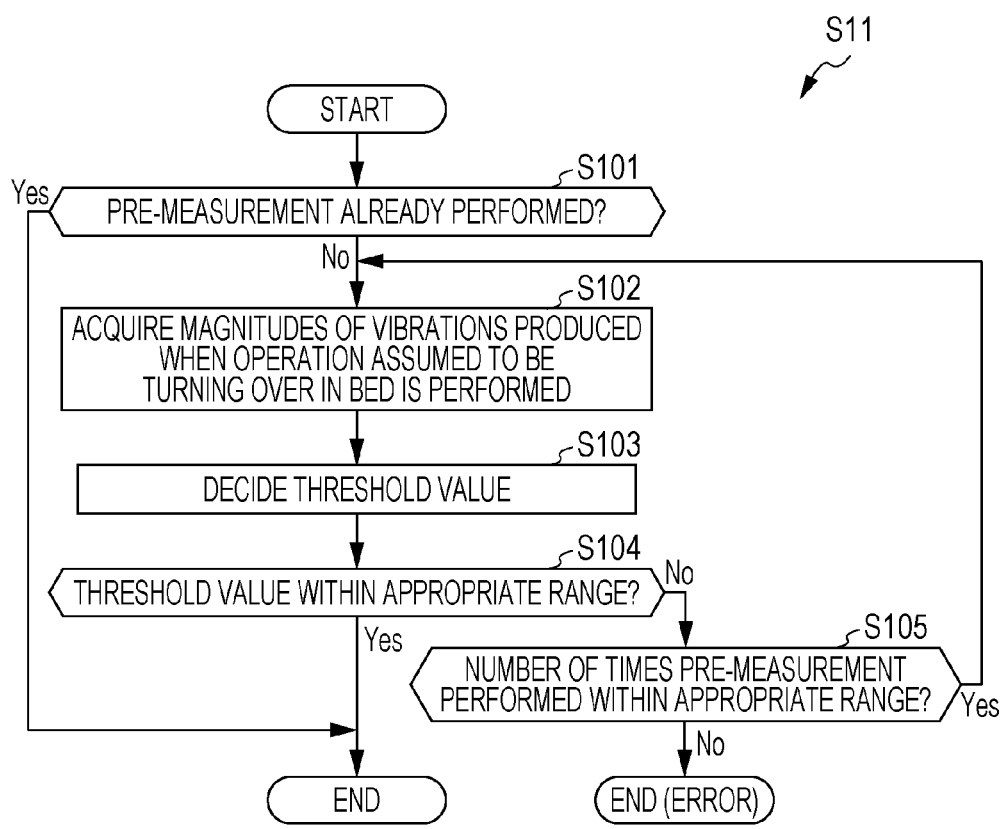
FIG. 12 is a flow diagram depicting initialization processing in the embodiment.

FIG. 12 is a flow diagram depicting initialization processing in the present embodiment. The flow diagram depicted in FIG. 12 provides a detailed depiction of the processing included in the initialization processing S11 in FIG. 10.

In step S101, the body movement determination unit 22 determines whether or not pre-measurement has already been performed. In the case where it is determined that pre-measurement has already been performed (yes in step S101), the series of processing depicted in FIG. 12 ends. In the case where it is determined that pre-measurement has not yet been performed (no in step S101), processing advances to step S102.

In step S102, the body movement determination unit 22 causes the user U to perform a movement that is assumed to be turning over in bed, and acquires a time series of the magnitudes of vibrations acquired by the vibration sensor 15 when the movement that is assumed to be turning over in bed is performed by the user U. A movement that is assumed to be turning over in bed is, for example, a movement with which the user U turns his/her body from a face-up position to a face-down position (or from a face-down position to a face-up position) on the bedding B while awake. It should be noted that, in order to cause the user U to perform the abovementioned movement, for example, audio guidance such as "please turn over in bed" may be given to the user U.

In step S103, the body movement determination unit 22 decides the threshold value to be used in the body movement presence/absence determination processing, on the basis of the time series of the magnitudes of vibrations acquired in step S102. At such time, the threshold value is decided by selecting a threshold value with which the number of magnitudes exceeding the threshold value, from among the magnitudes of vibrations included in the time series acquired in step S102, becomes a predetermined number (for example, 20).

In step S104, the body movement determination unit 22 determines whether or not the threshold value decided in step S103 is within an appropriate range. The upper limit and the lower limit of the appropriate range may be determined as absolute values of the magnitudes of vibrations, or may be determined as a multiple C (C being a number smaller than 1, for example, ½ or ⅓) of the largest value of the magnitudes of vibrations included in the time series acquired in step S102.

In step S104, in the case where it is determined that the threshold value is within the appropriate range (yes in step S104), the series of processing depicted in FIG. 12 ends. In the case where it is determined that the threshold value has deviated from the appropriate range (no in step S104), processing advances to step S105.

In step S105, the body movement determination unit 22 determines whether or not the number of times that pre-measurement has been performed up to that point in time is within an appropriate range (for example, approximately five times). In the case where the number of times that pre-measurement has been performed is within the appropriate range (yes in step S105), step S102 is executed once again. In the case where the number of times that pre-measurement has been performed has deviated from the appropriate range (no in step S105), the series of processing depicted in FIG. 12 ends. It should be noted that, in this case, a code indicating that the initialization processing cannot be ended properly (an error code, so to speak) may be provided to another execution unit (an execution process or the like) being executed by the information terminal device 10.

Figure 13:
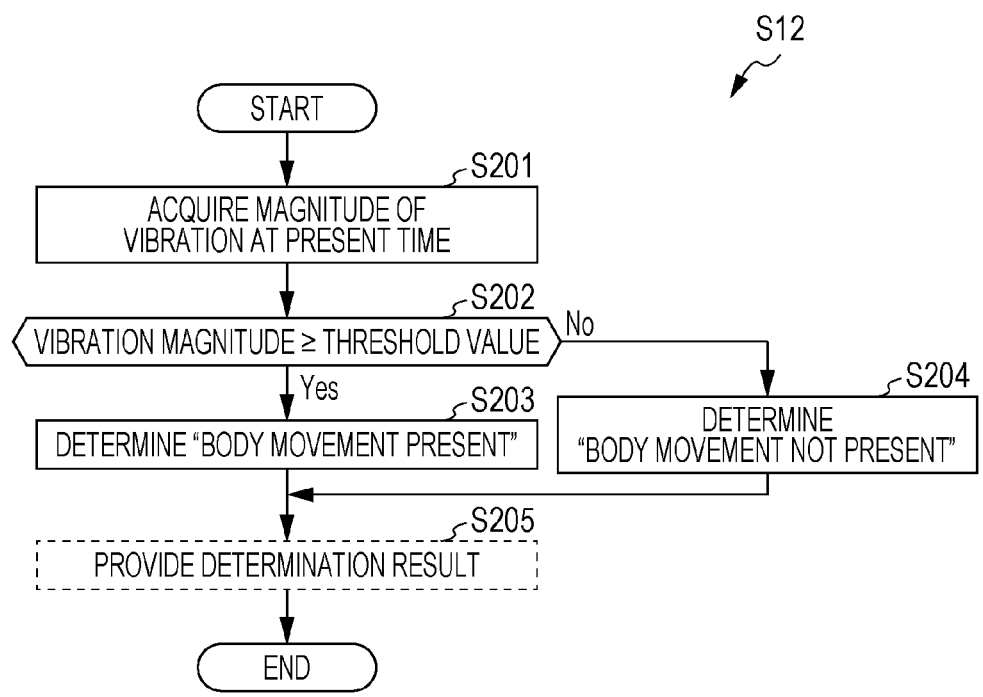
FIG. 13 is a flow diagram depicting body movement presence/absence determination processing in the embodiment.

FIG. 13 is a flow diagram depicting body movement presence/absence determination processing in the present embodiment. The flow diagram depicted in FIG. 13 provides a detailed depiction of the processing included in the body movement presence/absence determination processing S12 in FIG. 10.

In step S201, the body movement determination unit 22 acquires the magnitude of the vibration detected by the vibration sensor 15 at the present point in time.

In step S202, the body movement determination unit 22 determines whether or not the magnitude of the vibration at the present point in time acquired in step S201 is equal to or greater than the threshold value. In the case where it is determined that the magnitude of the vibration at the present point in time is equal to or greater than the threshold value (yes in step S202), the body movement determination unit 22 determines "body movement present" (step S203). However, in the case where it is determined that the magnitude of the vibration at the present point in time is less than the threshold value (no in step S202), the body movement determination unit 22 determines "body movement not present" (step S204).

It should be noted that the body movement determination unit 22 may determine "body movement present" in the case where reference is made to determination results of a predetermined number of times in the past and the magnitudes of the vibrations have been continuously equal to or greater than the threshold value for a plurality of times up to the present point in time.

In step S205, the body movement determination unit 22 provides the determination result of step S203 or S204 to another functional block or the like provided in the information terminal device 10. For example, in a scenario in which the information terminal device 10 is used to control the operation of an air conditioner on the basis of whether or not there is a body movement, the body movement determination unit 22 provides the determination result to an air conditioner control processing unit (not depicted) that controls the air conditioner. In this case, the air conditioner control processing unit turns on the air conditioning control of the air conditioner in the case where a "body movement present" determination result has been acquired from the body movement determination unit 22 a predetermined number of times or more within a predetermined time. It should be noted that the processing of step S205 is not an essential configuration in the present disclosure and may not be performed.

Figure 14:
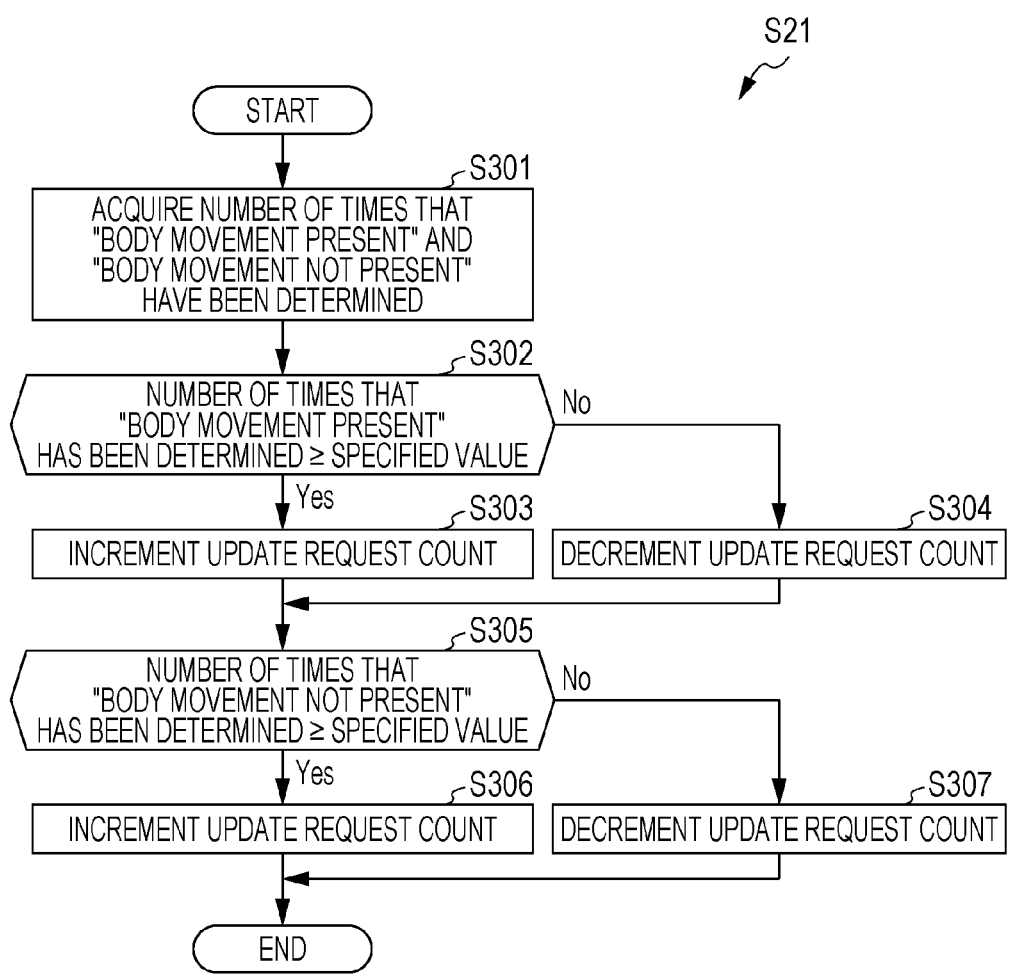
FIG. 14 is a flow diagram depicting update request count increase/decrease processing in the embodiment.

FIG. 14 is a flow diagram depicting update request count increase/decrease processing in the present embodiment. The flow diagram depicted in FIG. 14 provides a detailed depiction of the processing included in the update request count increase/decrease processing S21 in FIG. 11.

In step S301, the threshold value update unit 28 acquires the number of times that the body movement determination unit 22 has determined "body movement present" and "body movement not present" within the predetermined period. The predetermined period can be a period that corresponds to the cycles (one day or one week, for example) at which the threshold value update processing is performed, from the present point in time into the past, for example.

In step S302, the threshold value update unit 28 determines whether or not the number of times that the body movement determination unit 22 has determined "body movement present" is equal to or greater than a specified value. In the case where the number of times that "body movement present" has been determined is equal to or greater than the specified value in step S302 (yes in step S302), the update request count is incremented (step S303). However, in the case where the number of times that "body movement present" has been determined is less than the specified value in step S302 (no in step S302), the update request count is decremented (step S304).

In step S305, the threshold value update unit 28 determines whether or not the number of times that the body movement determination unit 22 has determined "body movement not present" is equal to or greater than the specified value. In the case where the number of times that "body movement not present" has been determined is equal to or greater than the specified value in step S305 (yes in step S305), the update request count is incremented (step S306). However, in the case where the number of times that "body movement not present" has been determined is less than the specified value in step S305 (no in step S305), the update request count is decremented (step S307).

Once steps S306 and S307 have ended, the series of processing depicted in FIG. 14 ends.

It should be noted that, in steps S304 and S307, the update request count may be set to the initial value in the case where the number of times that "body movement present" or "body movement not present" has been determined is less than the specified value.

Figure 15:
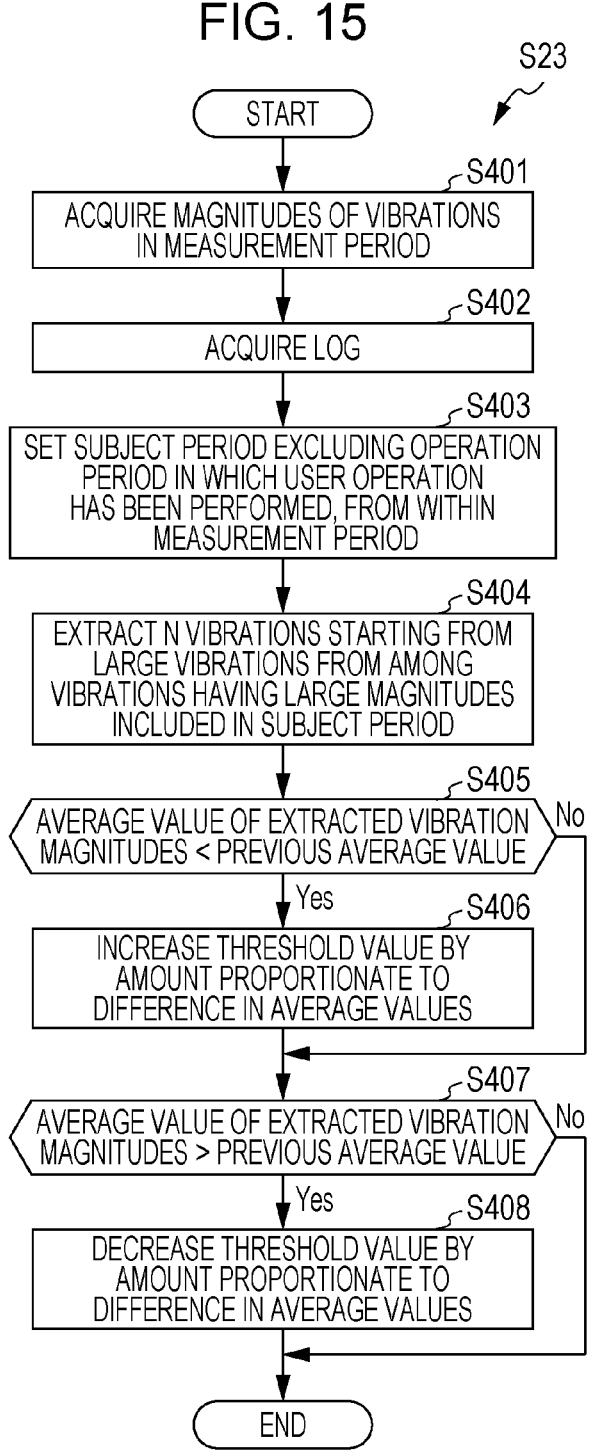
FIG. 15 is a flow diagram depicting threshold value update processing in the embodiment.

FIG. 15 is a flow diagram depicting threshold value update processing in the present embodiment. The flow diagram depicted in FIG. 15 provides a detailed depiction of the processing included in the threshold value update processing S23 in FIG. 11.

In step S401, the threshold value update unit 28 acquires a time series of the magnitudes of vibrations from within a predetermined measurement period from the vibration data accumulation unit 27. This time series of the magnitudes of vibrations is obtained by the vibration data acquisition unit 26 repeatedly acquiring the magnitudes of vibrations detected by the vibration sensor 15 and storing the acquired magnitudes in the vibration data accumulation unit 27.

In step S402, the threshold value update unit 28 acquires the extraction log 50 from the log accumulation unit 25.

In step S403, the exclusion unit 29 sets a subject period excluding an operation period in which an operation by the user U has been performed, from within the measurement period. The method for setting the subject period is as depicted in FIG. 7(a), for example.

In step S404, the threshold value update unit 28 extracts N number of magnitudes starting from large magnitudes from among the magnitudes of vibrations included in the time series acquired in step S401 and included in the subject period. Here, N is 100, for example. It should be noted that, here, N number of magnitudes may be extracted starting from large magnitudes, after M number of magnitudes have been excluded starting from large magnitudes, from among the magnitudes of vibrations included in the subject period. This is because there is a possibility that the M pieces of vibration data may include abnormal values. M is 10, for example.

It should be noted that reading out the N pieces of separately stored vibration data corresponds to the above-mentioned extraction in the case where N pieces of vibration data have been separately stored starting from vibration data having large vibration magnitudes when the vibration data acquisition unit 26 stores vibration data in the vibration data accumulation unit 27.

In step S405, the threshold value update unit 28 determines whether or not the average value of the magnitudes of the vibrations extracted in step S404 (hereinafter, also referred to as the "present average value") is lower than the average value of the magnitudes of the vibrations extracted in step S404 when the series of processing depicted in FIG. 15 was previously performed (hereinafter, also referred to as the "previous average value"). In the case where it is determined in step S405 that the present average value is lower than the previous average value (yes in step S405), the threshold value is increased by an amount proportionate to the difference between the present average value and the previous average value (step S406).

In step S407, the threshold value update unit 28 determines whether or not the present average value is higher than the previous average value. In the case where it is determined in step S407 that the present average value is higher than the previous average value (yes in step S407), the threshold value is decreased by an amount proportionate to the difference between the present average value and the previous average value (step S408).

In this way, the threshold value update unit 28 updates the threshold value on the basis of the present average value and the previous average value.

As mentioned above, the information terminal device of the present embodiment updates the threshold value that is used to determine a body movement of a user on the basis of vibration data having excluded therefrom vibration data of a period in which it is determined that the user operated the information terminal device, from among measured vibration data. The vibration data of the period in which it is determined that the user operated the information terminal device includes vibrations produced by an operation by the user, namely components of vibrations that are different from the body movements made during sleep by the user. Thus, by removing these components by means of the abovementioned method, the threshold value can be updated in an appropriate manner. As a result, it is possible to improve the precision of determining whether or not there is a body movement of the user by means of the information terminal device.

Furthermore, the information terminal device updates the threshold value further excluding vibration data of periods immediately before and immediately after the period in which it is determined that the user operated the information terminal device. In the period before the abovementioned period, there is a possibility that the user may have moved his/her body in order to search for and prepare to operate the information terminal device, and in the period after the abovementioned period, there is a possibility that the user may have moved his/her body in order to perform a movement to place the information terminal device on the bedding after having finished operating the information terminal device. Thus, components of vibrations that are different from the body movements made during sleep by the user are also included in the vibration data of the periods before and after the abovementioned period. Therefore, by removing these components by means of the abovementioned method, the threshold value can be updated in an even more appropriate manner.

Furthermore, the information terminal device updates the threshold value using vibration data having had further excluded therefrom vibration data of a period in which it is determined that the information terminal device was moved by the user away from on the bedding. The vibration data of the period in which it is determined that the information terminal device was away from on the bedding includes vibrations produced by an operation by the user, namely components of vibrations that are different from the body movements made during sleep by the user. Therefore, by removing these components by means of the abovementioned method, the threshold value can be updated in an even more appropriate manner.

Furthermore, the information terminal device updates the threshold value further excluding vibration data of periods immediately before and immediately after the period in which it is determined that the information terminal device was away from on the bedding. In the periods before and after the abovementioned period, there is a possibility that the user may hold the information terminal device and move his/her body in order to get out of bed or get into bed. Thus, components of vibrations that are different from the body movements made during sleep by the user are also included in the vibration data of the periods before and after the abovementioned period. Therefore, by removing these components by means of the abovementioned method, the threshold value can be updated in an even more appropriate manner.

Furthermore, the information terminal device, after determining whether or not there is a body movement of the user using the threshold value, increases or decreases the threshold value on the basis of the result of that determination. Even if the body movements performed by the user are the same, the way in which vibrations propagate changes when the bedding is changed or when the placement surface changes due to a change in the placement location on the bedding, and therefore it may no longer be possible to appropriately determine whether or not there is a body movement of the user with the previously used threshold value. In such a case, by obtaining an appropriate threshold value using a determination result indicating whether or not there is a body movement on the new bedding or the new placement location on the bedding, the threshold value can be updated in an even more appropriate manner.

Furthermore, the information terminal device can specifically specify the time at which an operation by the user has been performed with respect to the information terminal device on the basis of log information generated by an application unit.

Modified Example 1 of the Embodiment

Figure 16:
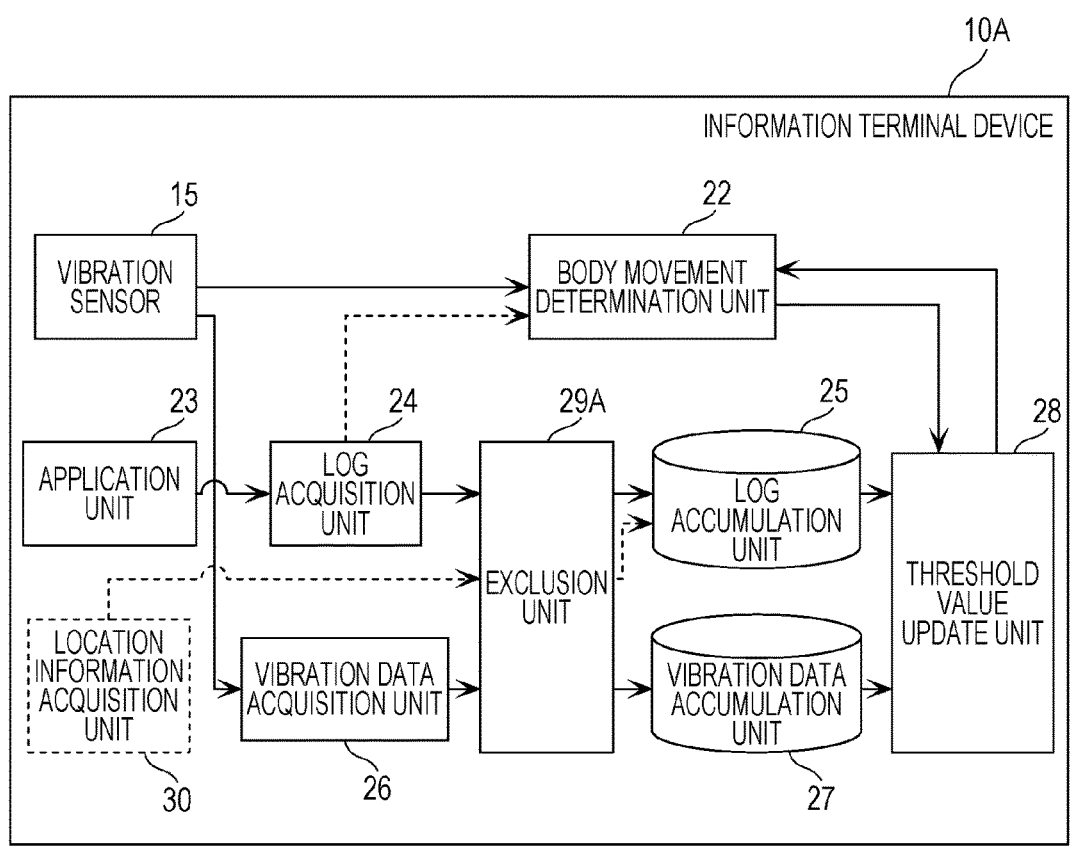
FIG. 16 is a block diagram depicting a functional configuration of an information terminal device in modified example 1 of the embodiment.

FIG. 16 is a block diagram depicting a functional configuration of an information terminal device 10A in the present modified example.

As depicted in FIG. 16, the information terminal device 10A is provided with the body movement determination unit 22, the application unit 23, the log acquisition unit 24, the log accumulation unit 25, the vibration data acquisition unit 26, the vibration data accumulation unit 27, the threshold value update unit 28, and an exclusion unit 29A. Furthermore, the information terminal device 10A may be provided with the location information acquisition unit 30.

The information terminal device 10A is different from the information terminal device 10 in the embodiment with regard to the location in which the exclusion unit 29A is arranged. In other words, the exclusion unit 29A is arranged at a stage after the log acquisition unit 24 and the vibration data acquisition unit 26, and before the log accumulation unit 25 and the vibration data accumulation unit 27.

The exclusion unit 29A is a processing unit that excludes a portion of the extraction logs accumulated in the log accumulation unit 25 by the log acquisition unit 24, and excludes a portion of the vibration data accumulated in the vibration data accumulation unit 27 by the vibration data acquisition unit 26. When data is to be excluded, similar to the exclusion unit 29 of the embodiment, vibration data included in the operation period or the out-of-bed period from within the measurement period, or vibration data included in the predetermined period that includes the operation period or the out-of-bed period, is excluded.

As mentioned above, the information terminal device of the present modified example has an advantage in that it is possible to reduce the amount of logs stored in the log accumulation unit 25 and the vibration data accumulation unit 27.

Modified Example 2 of the Embodiment

Figure 17:
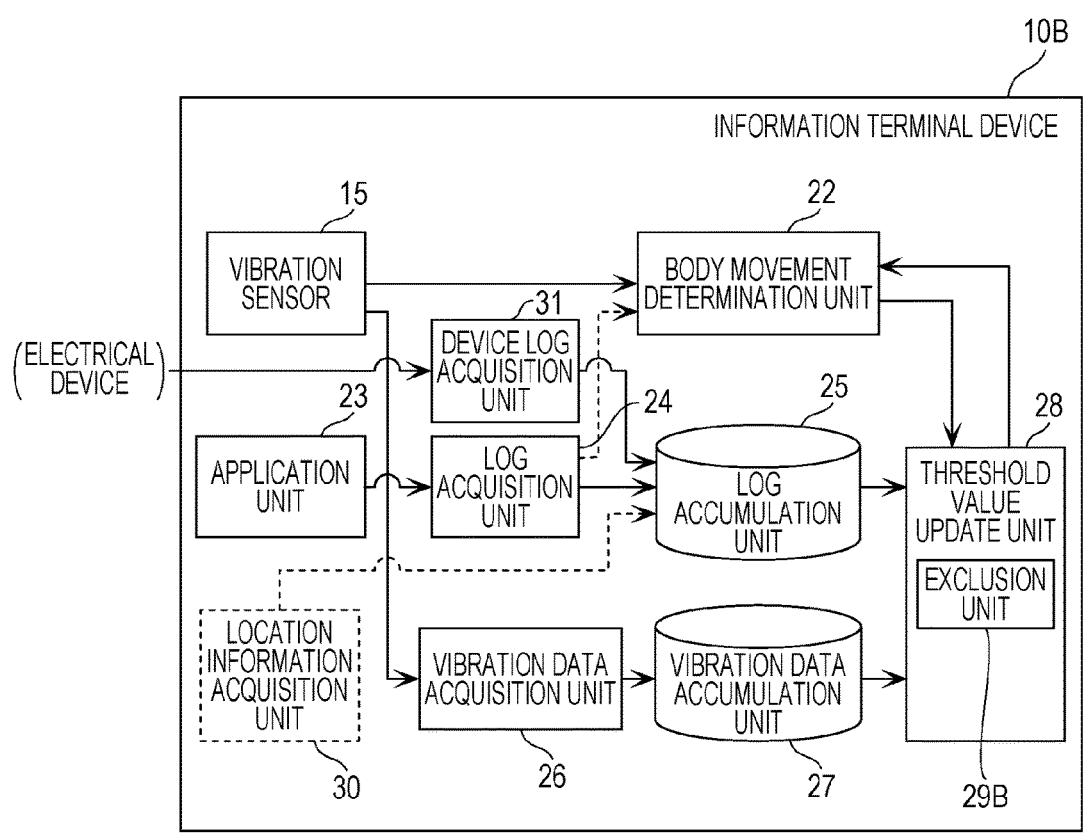
FIG. 17 is a block diagram depicting a functional configuration of an information terminal device in modified example 2 of the embodiment.

FIG. 17 is a block diagram depicting a functional configuration of an information terminal device 10B in the present modified example.

As depicted in FIG. 17, the information terminal device 10B is provided with the body movement determination unit 22, the application unit 23, the log acquisition unit 24, the log accumulation unit 25, the vibration data acquisition unit 26, the vibration data accumulation unit 27, the threshold value update unit 28, and a device log acquisition unit 31. Furthermore, the threshold value update unit 28 has an exclusion unit 29B.

Compared to the information terminal device 10A of the embodiment, the information terminal device 10B is different in being provided with the device log acquisition unit 31 and the exclusion unit 29B. It should be noted that, similar to the information terminal device 10A of the embodiment, the information terminal device 10B may have a hardware configuration that is the same as a general information terminal device (a smartphone, a mobile telephone terminal, or the like) provided with a vibration sensor, or may be a dedicated device (also referred to as a body movement measuring device) provided with a general vibration sensor.

The device log acquisition unit 31 is a processing unit that acquires log information of a device that is external to the information terminal device 10B, by way of the communication IF 14. The external device here may be an electrical device in the house in which the bedding B is arranged. The electrical device in the house is a light, a restroom toilet seat, a washing machine, a refrigerator, or the like installed in a room, a corridor, a restroom, or the like. The device log acquisition unit 31 acquires a device operation time, which is the time at which an operation by the user U with respect to the electrical device has been performed, and stores the acquired device operation time in the log accumulation unit 25.

The exclusion unit 29B performs the same operation as the exclusion unit 29 in the abovementioned embodiment, and additionally performs the following operation. The exclusion unit 29B specifies a device operation period in which the user performed the operation with respect to the electrical device in a house in which the bedding is arranged. The exclusion unit 29B may specify the device operation period based on the device operation time stored in the log accumulation unit 25. The exclusion unit 29B excludes one or pieces of vibration data (referred to as third vibration data), associated with the vibration times included in the device operation period, from the plural pieces of vibration data in the measurement period.

The threshold value update unit 28 updates the threshold value using the plurality of pieces of vibration data from which the one or more pieces of third vibration data are further excluded. Also, the exclusion unit 29 may update the threshold value using the plurality of pieces of vibration data from which the one or more pieces of third vibration data are further excluded.

The exclusion unit 29 may further exclude one or more pieces of vibration data (referred to as fourth vibration data), associated with vibration time which is included in at least one of periods immediately before and immediately after the device operation period, from the plurality of pieces of vibration data. The threshold value update unit 28 updates the threshold value using the plurality of pieces of vibration data from which the one or more pieces of the fourth vibration data are further excluded. Also, the exclusion unit 29 may update the threshold value using the plurality of pieces of vibration data from which the one or more pieces of fourth vibration data are further excluded.

It should be noted that, in the present modified example, the information terminal device 10B may be a smartwatch or a wristband-type of activity meter, for example, and the external electrical device may be a smartphone. By implementing this kind of configuration, for example, it is possible to remove, from vibration data, components of vibrations produced by the smartwatch or wristband-type of activity meter due to operations that can be performed in a smartphone such as replying to received mails, in addition to components of vibrations produced by operations that can be performed in the smartwatch or wristband-type of activity meter such as confirming mail reception notifications and confirming received mail content.

As mentioned above, the information terminal device of the present embodiment updates the threshold value using vibration data having had further excluded therefrom vibration data of a period in which it is determined that the user operated an electrical device in the house. The vibration data of the period in which it is determined that the user operated the electrical device includes vibrations produced by the operation by the user, namely components of vibrations that are different from the body movements made during sleep by the user. Therefore, by removing these components by means of the abovementioned method, the threshold value can be updated in an even more appropriate manner.

For example, by removing vibration data of the smartphone in a period such as from a light in a room, corridor, or restroom being turned on to being turned off, from sitting on to rising from a restroom toilet seat, from the setting of a washing machine being started to washing being started, or from the door of a refrigerator being opened to being closed, it is possible to remove, from vibration data, vibration components produced by the user operating the electrical device in the house, in addition to components of vibrations produced by operations such as voice calling and transmitting/receiving mail that the user is able to perform with a smartphone.

Furthermore, the information terminal device updates the threshold value further excluding vibration data of periods before and after the period in which it is determined that the user operated the electrical device. In the period before the abovementioned period, there is a possibility that the user may have moved his/her body in order to search for and prepare to operate a remote control for the electrical device, and in the period after the abovementioned period, there is a possibility that the user may have moved his/her body in order to perform a movement to place the remote control in a predetermined location after having finished operating the remote control. Thus, components of vibrations that are different from the body movements made during sleep by the user are also included in the vibration data of the periods before and after the abovementioned period. Therefore, by removing these components by means of the abovementioned method, the threshold value can be updated in an even more appropriate manner.

Modified Example 3 of the Embodiment

In the present modified example, a description will be given regarding a technique with which an information terminal device additionally presents the user with an image indicating vibration magnitude. It should be noted that the hardware configuration and functional configuration of the information terminal device according to the present modified example are the same as those of the information terminal device 10 of the embodiment.

The information terminal device 10 according to the present modified example generates an image indicating time series data for magnitudes of vibrations in the measurement period, and displays the image by means of the display device 16. The user U, by seeing the image displayed on the display device 16, is thereby able to know whether or not his/her body has moved from the magnitudes of the vibrations in the measurement period.

Figure 18:
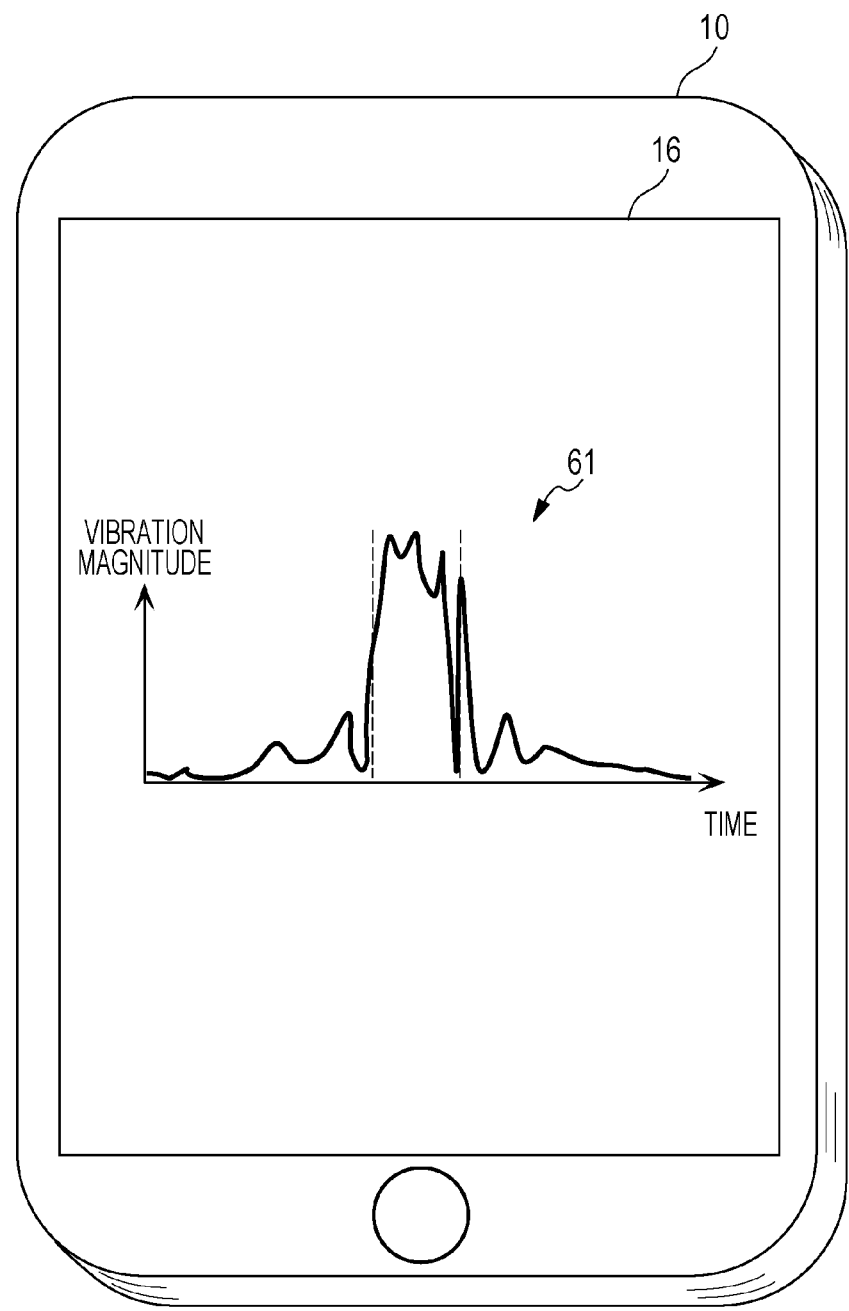
FIG. 18 is a block diagram depicting a first example of a display image of an information terminal device in modified example 3 of the embodiment.

FIG. 18 is a block diagram depicting a first example of a display image of the information terminal device 10 in modified example 3 of the embodiment.

As depicted in FIG. 18, the display device 16 displays an image 61 that includes a graph indicating a time series of the magnitudes of vibrations in the measurement period. The graph included in the image 61 indicates a time series of the magnitudes of vibrations across the entirety of the measurement period or in a portion of time from within the measurement period, with the horizontal axis representing time and the vertical axis representing the magnitudes of vibrations.

The user U sees the image 61 displayed by the information terminal device 10, and is thereby able to visually perceive whether or not his/her body has moved during sleep, the times at which there have been body movements, cycles of body movements, and the like. It is therefore possible, for example, for the information terminal device 10 to also be useful for health management, such as discovering changes in the physical condition of the user U early on.

Figure 19:
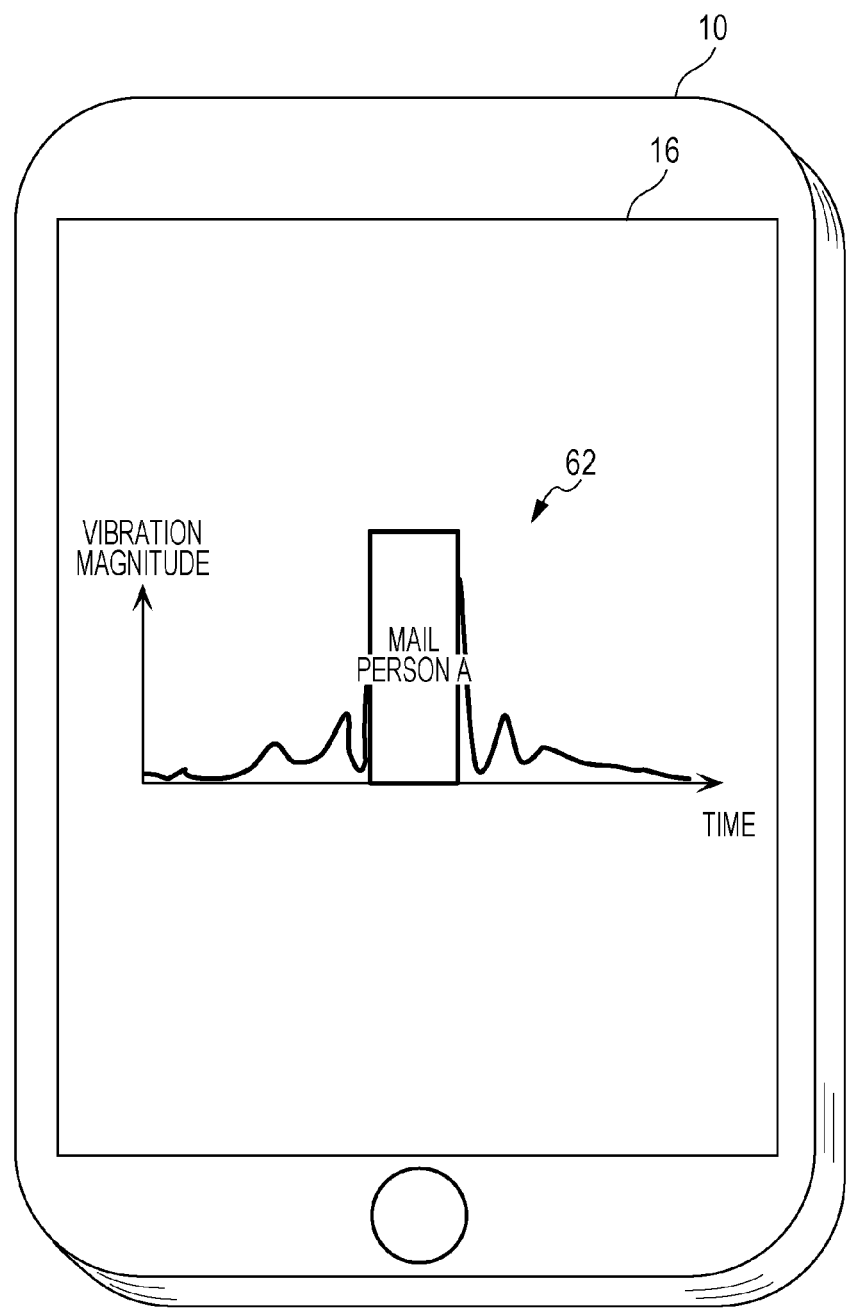
FIG. 19 is a block diagram depicting a second example of a display image of an information terminal device in modified example 3 of the embodiment.

FIG. 19 is a block diagram depicting a second example of a display image of the information terminal device 10 in modified example 3 of the embodiment.

As depicted in FIG. 19, the display device 16 displays an image 62 that includes a graph indicating a time series of the magnitudes of vibrations in the measurement period. The graph included in the image 62 is the same as the graph included in the image 61, apart from a graphic being included in a portion corresponding to a period in which vibrations exceeded the threshold value, and the processing performed by the information terminal device 10 in that period being indicated by means of characters such as "Mail/Person A".

The user U sees the image 62 displayed by the information terminal device 10, and is thereby able to know whether or not his/her body has moved during sleep and so forth, and also processing by the information terminal device 10 that has been performed on the basis of an operation implemented by the user U during a break in sleeping. Thus, the user U is able to visually perceive an operation performed by him/her with respect to the information terminal device 10 during a break in sleeping, and the processing performed by the information terminal device 10 on the basis of that operation.

As mentioned above, according to the information terminal device of the present embodiment, the user is able to visually perceive health management that is based upon whether or not his/her body has moved during sleep, and actions performed by himself/herself during a break in sleeping.

It should be noted that, in the aforementioned embodiments, the constituent elements may be configured by using dedicated hardware, or may be realized by executing a software program suitable for the constituent elements. The constituent elements may be realized by a program execution unit such as a CPU or a processor reading out and executing a software program recorded in a recording medium such as a hard disk or a semiconductor memory. Here, software that realizes a body movement measuring device of the aforementioned embodiments is a program such as the following.

Specifically, this program causes a computer corresponding to an information terminal device to executes: determining whether or not there is a body movement of a user on bedding on which the computer has been placed, based on whether or not a magnitude of a vibration indicated by vibration data detected by a vibration sensor of the computer that detects vibrations of the computer is equal to or greater than a threshold value; acquiring the vibration data indicating the magnitude of the vibration detected by the vibration sensor, and a vibration time indicating a time at which the vibration sensor detected the vibration; associating the vibration data with the vibration time; storing the vibration data and the vibration time in a memory of the computer; acquiring log information including a time at which an operation by the user was performed with respect to the computer; storing the acquired log information in the memory; excluding one or more pieces of first vibration data from a plurality of pieces of vibration data stored in the memory, wherein the plurality of pieces of vibration data are acquired within one period, wherein vibration times associated with the one or more pieces of first vibration data are included in an operation period in which the user performed the operation with respect to the information terminal device, and wherein the operation period is specified based on the time in the log information stored in the memory; and updating the threshold value using at least one piece of vibration data in the plurality of pieces of vibration data from which the one or more pieces of first vibration data are excluded.

An information terminal device and the like according to one or more aspects have been described hereinabove on the basis of the embodiments; however, the present disclosure is not restricted to these embodiments. Modes in which various modifications conceived by a person skilled in the art have been implemented in the present embodiments, and modes constructed by combining the constituent elements in different embodiments may also be included within the scope of one or more aspects provided they do not depart from the purpose of the present disclosure.

The present disclosure can be used for a body movement measuring device that measures body movements, a control device that controls another device on the basis of the detection of body movements, and the like.

What is claimed is:

1. A control method of an information terminal device provided with a vibration sensor, a processor, and a memory, the control method causes the processor to execute:
   first measuring, by the vibration sensor, magnitudes of a plurality of vibrations of the information terminal placed on a bedding during a first period;
   determining, by the processor, whether or not there is a body movement of a user on the bedding based on whether or not the magnitude of a vibration of the information terminal device is equal to or greater than a threshold value;
   acquiring, by the processor, the magnitude of the vibration of the information terminal device detected by the vibration sensor, and a vibration time indicating a time at which the vibration sensor detected the vibration of the information terminal device;
associating, by the processor, the vibration time with the magnitude of the vibration;
storing a plurality of pieces of vibration data that include the magnitude of the vibration and the associated vibration time in the memory;
acquiring, by the processor, log information including a time at which an operation by the user was performed with respect to the information terminal device;
storing the log information in the memory,
modifying, by the processor, the stored plurality of pieces of vibration data by excluding one or more pieces of first vibration data corresponding to a target vibration time period from the plurality of pieces of vibration data stored in the memory such that the modified pieces of vibration data include less data than the stored plurality of pieces of vibration data,
wherein
the target vibration time period includes an operation period in which the user performed the operation with respect to the information terminal device,
the target vibration time period includes a start time point and ending time point,
the start time point being when the user starts performing the operation with respect to the information terminal device, and
the operation period is specified based on the time in the log information stored in the memory;
updating the threshold value using the plurality of pieces of vibration data from which the one or more pieces of first vibration data are excluded;
second measuring, by the vibration sensor, magnitudes of a plurality of vibrations of the information terminal placed on the bedding during a second period; and
determining, by the processor, whether or not there is a body movement of the user on the bedding based on whether or not one or more of the magnitudes of the plurality of vibrations of the information terminal device measured during the second period is equal to or greater than the updated threshold value.

2. The control method according to claim 1,
wherein, in the modifying, one or more pieces of second vibration data are further excluded from the plurality of pieces of vibration data, wherein vibration times associated with the one or more pieces of second vibration data are included in a period immediately before or immediately after the operation period, and
wherein, in the updating, the threshold value is updated using the plurality of pieces of vibration data from which the one or more pieces of second vibration data are further excluded.

3. The control method according to claim 1,
wherein the control method further causes the processor to execute:
acquiring a device operation time from an electrical device by way of a network, wherein the device operation time is a time at which an operation has been performed by the user with respect to the electrical device in a house in which the bedding is arranged; and
storing the device operation time in the memory,
wherein, in the modifying, one or more pieces of third vibration data are further excluded from the plurality of pieces of vibration data, wherein vibration times associated with the one or more pieces of third vibration data are included in a device operation period in which the user performed the operation with respect to the electrical device, and the device operation period is specified based on the device operation time stored in the memory, and
wherein, in the updating, the threshold value is updated using the plurality of pieces of vibration data from which the one or more pieces of third vibration data are further excluded.

4. The control method according to claim 3,
wherein, in the modifying, one or more pieces of fourth vibration data are further excluded from the plurality of pieces of vibration data, wherein vibration times associated with the one or more pieces of fourth vibration data are included in a period immediately before or immediately after the device operation period, and
wherein, in the updating, the threshold value is updated using the plurality of pieces of vibration data from which the one or more pieces of fourth vibration data are further excluded.

5. The control method according to claim 1,
wherein the control method further causes the processor to execute:
acquiring location information which indicates a location of the information terminal device; and
storing a location change time, which indicates a time at which the location of the information terminal device changed, calculated based on the acquired location information,
wherein, in the modifying, one or more pieces of fifth vibration data are further excluded from the plurality of pieces of vibration data, wherein vibration times associated with the one or more pieces of fifth vibration data are included in an out-of-bed period in which the information terminal device was located in a location that is different from on the bedding, and wherein the out-of-bed period is specified based on the location change time stored in the memory, and
wherein, in the updating, the threshold value is updated using the plurality of pieces of vibration data from which the one or more pieces of fifth vibration data are further excluded.

6. The control method according to claim 5,
wherein, in the modifying, one or more pieces of sixth vibration data are further excluded from the plurality of pieces of vibration data, wherein vibration times associated with the one or more pieces of sixth vibration data are included in a period immediately before or immediately after the out-of-bed period, and
wherein, in the updating, the threshold value is updated using the plurality of pieces of vibration data from which the one or more pieces of sixth vibration data are further excluded.

7. The control method according to claim 1,
wherein the processor repeats the determining,
wherein the threshold value is updated when a proportion of a number of times that the determination indicates a body movement of the user is present or absent, out of a number of times that the determination has been performed, has deviated from a predetermined appropriate range.

8. The control method according to claim 1,
wherein an application program is stored in the memory, and
wherein the control method further causes the processor to executes the application program, wherein the log information is generated by the executing application program when an operation by the user is performed with respect to the information terminal device.

9. A body movement measuring device, comprising:
a vibration sensor that
   detects vibrations of the body movement measuring device,
   measures magnitudes of a plurality of vibrations of the body movement measuring device placed on a bedding during a first period, and
   measures magnitudes of a plurality of vibrations of the body movement measuring device placed on a bedding during a second period;
a memory; and
a processor which:
determines whether or not there is a body movement of a user on the bedding based on whether or not the magnitude of a vibration indicated by vibration data detected by the vibration sensor during the first period is equal to or greater than a threshold value;
acquires the vibration data indicating the magnitude of the vibration detected by the vibration sensor, and a vibration time indicating a time at which the vibration sensor detected the vibration;
associates the vibration time with the magnitude of the vibration;
stores a plurality of pieces of vibration data that include the vibration time and the associated magnitude of the vibration in the memory;
acquires log information including a time at which an operation by the user was performed with respect to the body movement measuring device;
stores the log information in the memory;
modifies the stored plurality of pieces of vibration data by excluding one or more pieces of first vibration data corresponding to a target vibration time period from the plurality of pieces of vibration data stored in the memory such that the modified pieces of vibration data include less data than the stored plurality of pieces of vibration data,
wherein
the target vibration time period includes an operation period in which the user performed the operation with respect to the body movement measuring device,
the target vibration time period includes a start time point and ending time point,
the start time point being when the user starts performing the operation with respect to the information terminal device, and
the operation period is specified based on the time in the log information stored in the memory;
updates the threshold value using at least one piece of vibration data in the plurality of pieces of vibration data from which the one or more pieces of first vibration data are excluded; and
determines whether or not there is a body movement of the user on the bedding based on whether or not one or more of the magnitudes of the plurality of vibrations of the body movement measuring device measured during the second period is equal to or greater than the updated threshold value.

10. A non-transitory recording medium recording a program, the program causing a computer to executes:
first measuring, by a vibration sensor of the computer, magnitudes of a plurality of vibrations of the computer placed on a bedding during a first period;
determining, by a processor of the computer, whether or not there is a body movement of a user on the bedding based on whether or not the magnitude of a vibration of the computer is equal to or greater than a threshold value;
acquiring, by the processor, the magnitude of the vibration detected by the vibration sensor, and a vibration time indicating a time at which the vibration sensor detected the vibration;
associating, by the processor, the magnitude of the vibration with the vibration time;
storing a plurality of pieces of vibration data that include the magnitude of the vibration and the vibration time in a memory of the computer;
acquiring, by the processor, log information including a time at which an operation by the user was performed with respect to the computer;
storing the acquired log information in the memory;
modifying, by the processor, the stored plurality of pieces of vibration data by excluding one or more pieces of first vibration data corresponding to a target vibration time period from the plurality of pieces of vibration data stored in the memory such that the modified pieces of vibration data include less data than the stored plurality of pieces of vibration data,
wherein
the target vibration time period includes an operation period in which the user performed the operation with respect to the computer,
the target vibration time period includes a start time point and ending time point,
the start time point being when the user starts performing the operation with respect to the information terminal device, and
the operation period is specified based on the time in the log information stored in the memory;
updating the threshold value using at least one piece of vibration data in the plurality of pieces of vibration data from which the one or more pieces of first vibration data are excluded;
second measuring, by the vibration sensor, magnitudes of a plurality of vibrations of the information terminal placed on the bedding during a second period; and
determining, by the processor, whether or not there is a body movement of the user on the bedding based on whether or not one or more of the magnitudes of the plurality of vibrations of the computer measured during the second period is equal to or greater than the updated threshold value.

* * * * *